United States Patent [19]

Zipplies et al.

[11] Patent Number: 5,051,409
[45] Date of Patent: Sep. 24, 1991

[54] 2-AMINODECALIN DERIVATIVES AND THEIR USE

[75] Inventors: Matthias Zipplies, Hirschberg; Bernhard Zipperer, Dirmstein; Hubert Sauter, Mannheim; Norbert Goetz, Worms; Franz Roehl, Ludwigshafen; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 430,585

[22] Filed: Nov. 1, 1989

[30] Foreign Application Priority Data

Nov. 15, 1988 [DE] Fed. Rep. of Germany ....... 3838631

[51] Int. Cl.$^5$ .................... A01N 33/04; C07C 211/38
[52] U.S. Cl. .................................... 514/63; 514/319; 514/378; 514/406; 514/427; 514/429; 514/510; 514/544; 514/546; 514/644; 514/654; 514/655; 514/657; 546/205; 546/206; 548/247; 548/378; 548/400; 548/561; 548/565; 556/413; 556/418; 556/423; 560/107; 560/256; 564/374; 564/389; 564/390; 564/391; 564/454; 564/455; 564/456; 564/460
[58] Field of Search .............. 546/205, 206; 548/247, 548/378, 400, 561, 565; 556/413, 418, 423; 560/107, 256; 564/374, 389, 390, 391, 454, 455, 456, 460; 514/63, 319, 378, 406, 427, 429, 510, 544, 546, 644, 654, 655, 657

[56] References Cited

U.S. PATENT DOCUMENTS

| 2,894,659 | 2/1989 | Weissmuller et al. ........... 514/237.8 |
| 4,024,274 | 5/1977 | Druckrey et al. ............... 564/389 X |
| 4,214,094 | 7/1980 | Kamiya et al. ................. 564/389 X |
| 4,332,807 | 6/1982 | Belanger et al. ............... 564/389 X |
| 4,822,822 | 4/1989 | Arita et al. ..................... 564/387 x |
| 4,939,148 | 7/1990 | Statz et al. .................... 564/387 X |

FOREIGN PATENT DOCUMENTS

| 254150 | 1/1988 | European Pat. Off. . |
| 0309913 | 9/1988 | European Pat. Off. . |
| 0309914 | 9/1988 | European Pat. Off. . |
| 0355544 | 2/1990 | European Pat. Off. . |

Primary Examiner—Richard L. Raymond
Attorney, Agent, or Firm—Oblon, Spivak, McClelland, Maier & Neustadt

[57] ABSTRACT

2-Aminodecalin derivatives of the formula I

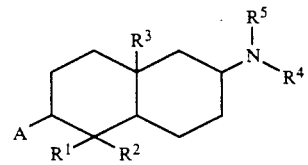

where
$R^1$, $R^2$ and $R^3$ are H or methyl,
A is H, OH, O-alkylcarbonyl, O-benzoyl or O-CH$_3$,
$R^4$ is H, cyclopropyl, alkyl, alkenyl, or alkynyl,
$R^5$ is alkyl, alkenyl or alkynyl which is substituted or unsubstituted,
cycloalkyl or cycloalkenyl whic is substituted or unsubstituted, substituted phenylalkyl, substituted cycloalkyl-alkyl, substituted 5-membered heterocyclic ring, bicycloalkyl-alkyl or
$R^4$ and $R^5$, together with the nitrogen atom, are a substituted or unsubstituted, saturated or unsaturated piperidine radical, their plant-tolerated salts and N-oxides, and fungicides containing these compounds.

8 Claims, No Drawings

2-AMINODECALIN DERIVATIVES AND THEIR USE

The present invention relates to N-substituted 2-aminodecalin derivatives, processes for their preparation, their use as fungicides, fungicidal mixtures and methods for controlling fungi with these active ingredients.

The compound 2-aminodecalin is known (Leroux, Comptes rendus de l'Academie de Sciences 141, 47; Leroux, Annales de Chimie et de Physique 21, 533). The four possible diastereomers of 2-aminodecalin have likewise been described in the literature (Hückel, Liebigs Ann. der Chemie 533 (1938), 14; Dauben et al., J. Amer. Chem. Soc. 76 (1954), 4420). The infrared spectra of N-methyl- and N,N-dimethyldecalylamine diastereomers have also been described (Feltkamp, Liebigs Ann. Chem. 683 (1965), 49-54). The synthesis of N-ethyldecalylamine has also been described in the literature (T. Pienemann et al., Synthesis 1987, 1005).

However, nothing is known about a fungicidal action of the compounds mentioned.

European Patent 254,150 describes the decalylalkylmorpholine derivative VII as being a compound having a fungicidal action.

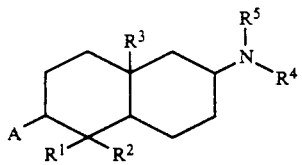

We have found that 2-aminodecalin derivatives of the formula I

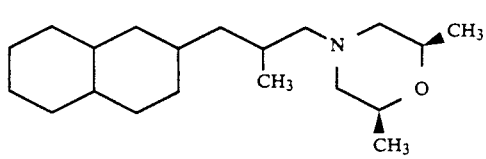

where $R^1$, $R^2$ and $R^3$ are identical or different and are each H or methyl, A is H, OH, O-$C_1$-$C_4$-alkylcarbonyl, O-benzoyl or O—$CH_3$, $R^4$ is H, $C_1$-$C_4$-alkyl, $C_2$-$C_4$-alkenyl, $C_3$- or $C_4$-alkynyl or cyclopropyl, $R^5$ is $C_3$-$C_{18}$-alkyl, $C_3$-$C_{18}$-alkenyl or $C_3$-$C_{18}$-alkynyl which is unsubstituted or monosubstituted to trisubstituted by $C_1$-$C_8$-alkoxy, $C_5$-$C_{12}$-cycloalkyl or $C_5$-$C_{12}$-cycloalkenyl which is unsubstituted or monosubstituted to trisubstituted by $C_3$-$C_8$-alkyl, $C_3$-$C_8$-alkenyl or $C_3$-$C_8$-alkoxy, or $R^5$ is a radical

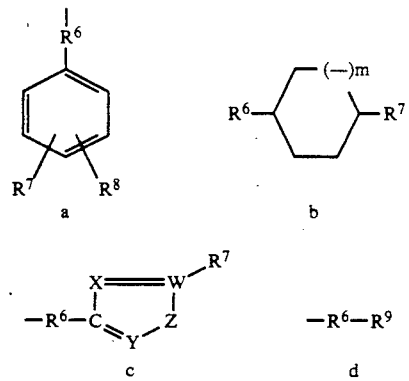

where $R^6$ is $C_1$-$C_5$-alkylene or $C_1$-$C_5$-alkenylene, $R^7$ is $C_3$-$C_8$-alkyl, $C_3$-$C_8$-alkenyl, $C_3$-$C_8$-alkoxy, $C_1$-$C_5$-alkoxy-$C_2$-$C_5$-alkyl, $C_3$-$C_5$-alkylthio or trimethylsilyl, $R^8$ is H or $CH_3$, $R^9$ is $C_6$-$C_{10}$-bicycloalkyl or $C_6$-$C_{10}$-bicycloalkenyl which is unsubstituted or substituted by 2 or 3 methyl groups, W, X, Y and Z are each a ring atom in an aromatic 5-membered heterocyclic ring, i.e. 1 or 2 radicals from the group consisting of O, S, N, NH, N—$R^7$ and 2 or 3 radicals CH and C—$R^7$, m is 0, 1 or 2, so that the radical 5b contains a cyclohexyl, cycloheptyl or cyclopentyl radical, $R^4$ and $R^5$, together with the nitrogen on which they are substituents, may furthermore form a 5-membered or 6-membered ring e or f

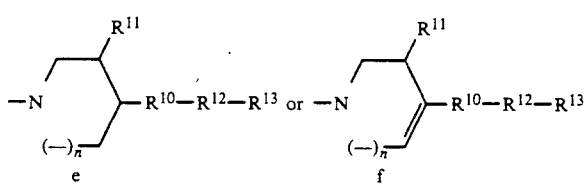

where $R^{10}$ is H or $(CH_2)_q$, in which q is 0, 1, 2, 3 or 4 or methyl, ethyl or branched $C_3$-$C_8$-alkyl, $R^{11}$ is H or $C_1$-$C_5$-alkyl, $R^{12}$ is H or phenyl when $R^{10}$ is not H, $R^{13}$ is $C_3$-$C_6$-alkyl when $R^{12}$ is phenyl and n is 0 or 1, so that the radical 5e or 5f contains a 6-membered or 5-membered heterocyclic ring, and their plant-tolerated salts and N-oxides are well tolerated by plants and have a powerful fungicidal action.

The present invention also relates to the trans-isomers and cis-isomers of the formula I and mixtures thereof. These compounds can be used as fungicides.

Preferred diasteriomers are those of the formula II

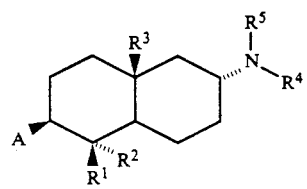

which are the trans-decalin derivatives having both the amino function and, where present, the radical A in the equatorial position.

For practical reasons, suitable active ingredients are also the salts of the novel decalylamines. These include the salts of the amines with any inorganic or organic acids or protic compounds in the widest sense, for example with hydrogen chloride, hydrogen bromide, hydrogen iodide, acetic acid, propionic acid, palmitic acid, stearic acid, perfluoroheptanoic acid, oxalic acid, malonic acid, benzoic acid, malic acid, dodecylsulfonic acid, alpha-naphthalenesulfonic acid, β-naphthalic acid, 2,6-dichloroisonicotinic acid, saccharin, salicylic acid, glycerol-2-phosphoric acid, methanesulfonic acid, dodecylbenzenesulfonic acid or p-toluenesulfonic acid.

$R^4$ is, for example, hydrogen, methyl, ethyl, propyl, isopropyl, n-butyl, isobutyl, sec-butyl, allyl, propargyl or cyclopropyl.

$R^5$ is, for example, branched or straight-chain $C_3-C_{18}$-alkyl, in particular $C_8-C_{16}$-alkyl, for example n-propyl, n-hexyl, n-heptyl, 4,4-dimethylpentyl, n-octyl, 6,6-dimethylhept-2-yl, n-nonyl, 3,5,5-trimethylhexyl, n-decyl, 3,7-dimethyloct-2-yl, n-undecyl, n-dodecyl, tridecyl, hexadecyl, octadecyl, 3,7-dimethyloctyl, 6,10-dimethylundec-2-yl, 2,3,5,5-tetramethylhexyl or 2,4,5,7,7-pentamethyloctyl, or $C_3-C_{18}$-alkenyl, such as $C_8-C_{12}$-alkenyl, for example 3,7-dimethyloct-6-enyl, or $C_3-C_{18}$-alkynyl, such as $C_6-C_{10}$-alkynyl, for example 4,4-dimethylpent-2-ynyl, or $C_3-C_{18}$-alkyl which is monosubstituted to trisubstituted by branched or straight-chain $C_1-C_8$-alkoxy, or $C_8-C_{16}$-alkyl, $C_3-C_{18}$-alkenyl or $C_3-C_{18}$-alkynyl, for example 4-methoxy-4-methylpentyl, 4-methoxy-4-methylpent-2-ynyl, 2-tert-butoxypropyl, 2-tert-amyloxypropyl, 3-tert-butoxy-2-methylbutyl or 3-tert-butoxypropyl.

$R^5$ may furthermore be $C_5-C_{12}$-cycloalkyl or $C_5-C_{12}$-cycloalkenyl which may be unsubstituted or monosubstituted to trisubstituted by branched or straight-chain $C_3-C_8$-alkyl, $C_3-C_8$-alkenyl or $C_3-C_8$-alkoxy, for example cyclohexyl, 4-tert-butylcyclohexyl, 4-isopropylcyclohexyl, 4-(2,4,4-trimethylpent-2-yl)-cyclohexyl, 4-tert-butoxycyclohexyl or 4-tert-butylcyclohexenyl; $R^5$ may furthermore be a radical a

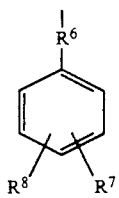

where
$R^6$ is branched or straight-chain $C_1-C_5$-alkylene or $C_2-C_5$-alkenylene, e.g. methylene,
$R^7$ is branched or straight-chain $C_3-C_8$-alkyl, $C_3-C_8$-alkenyl, $C_3-C_8$-alkoxy, $C_1-C_3$-alkoxy-$C_2-C_5$-alkyl, $C_3-C_5$-alkylthio, or the trimethylsilyl radical, for example tert-butyl,
and $R^8$ is hydrogen or methyl.

Examples of novel radicals of the structure a are 4-tert-butylbenzyl, 4-tert-butoxybenzyl, 4-trimethylsilylbenzyl, 4-tert-butylthiobenzyl, 4-tert-butylphenylethyl, 4-tert-butylphenylpropyl, 1-(4-tert-butylphenyl)-2-methylpropyl, 1-(4-tert-butyl-2-methylphenyl)-2-methylpropyl, 4-(2,3-dimethylbut-2-yl)-benzyl, 4-(2-methylbut-2-yl)-benzyl, 4-(2,4,4-trimethylpent-2-yl)-benzyl, 4-tert-butoxyphenylethyl and 4-(2-methoxyprop-2-yl)-benzyl; $R^5$ may furthermore be a radical b

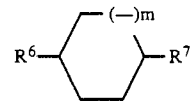

where $R^6$ and $R^7$ have the same meanings as above and m is 0, 1 or 2, so that the radical 5b contains a cyclohexyl, cycloheptyl or cyclopentyl radical.

Examples of radicals b are:

4-tert-butylcyclohexylmethyl,
4-tert-butoxycyclohexylmethyl and
1-(4-tert-butylcyclohexyl)-2-methylpropyl.

$R^5$ may furthermore be a radical c

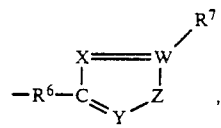

where $R^6$ and $R^7$ have the same meaning as above and W, X, Y and Z are the ring atoms in an aromatic 5-membered heterocyclic ring, i.e. 1 or 2 radicals from the group consisting of O, S, N, NH and N—$R^7$ and 2 or 3 radicals CH and C—$R^7$.

Examples of novel radicals c are:

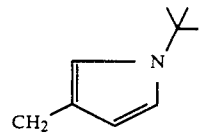

N-tert-butylpyrr-3-ylmethyl,

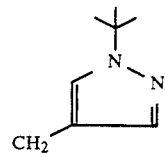

3-tert-butylisoxazol-5-ylmethyl

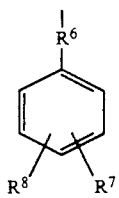

N-tert-butylpyrazol-4-ylmethyl.

$R^5$ may furthermore be a radical d $$-R^6-R^9 \quad\quad d$$

where $R^6$ has the same meaning as above but $R^9$ is a $C_6-C_{10}$-bicycloalkyl or $C_6-C_{16}$-bicycloalkenyl radical which is unsubstituted or substituted by 1-3 methyl groups.

Examples of the radical d are:

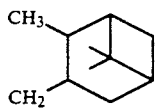

3,6,6-trimethyl[3.1.1.]bicyclohept-3-ylmethyl,

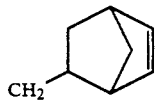

[2.2.1]bicyclohept-2-en-5-ylmethyl,

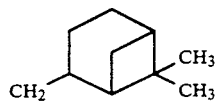

6,6-dimethyl[3.1.1]bicyclohept-2-ylmethyl and

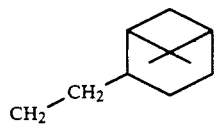

6,6-dimethyl[3.1.1]bicyclohept-2-ylethyl.

$R^4$ and $R^5$, together with the nitrogen atom on which they are substituents, may furthermore be a 5-membered or 6-membered ring (radicals e and f)

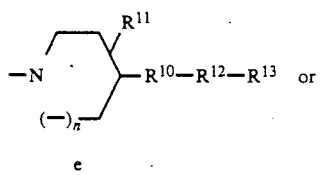

e

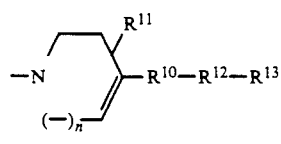

f where
- $R^{10}$ is hydrogen or the group $(CH_2)_q$, in which q is 0, 1, 2, 3 or 4, or methyl, ethyl or branched $C_3$-$C_8$-alkyl,
- $R^{11}$ is hydrogen or branched or straight-chain $C_1$-$C_5$-alkyl,
- $R^{12}$ is hydrogen or phenyl when $R^{10}$ is not H,
- $R^{13}$ is branched or straight-chain $C_3$-$C_6$-alkyl when $R^{12}$ is phenyl and
- n is 0 or 1, so that the radical 5e or 5f contains a 6-membered or 5-membered heterocyclic ring.

Examples of novel radicals e or f are: 4-methylpiperidinyl, 3,3-dimethylpiperidinyl, 3-ethyl-4-propylpiperidinyl, 4-phenylpiperidinyl, 4-benzylpiperidinyl, 4-(3-phenylpropyl)-piperidinyl, 4-[3-(4-tert-butylphenyl)-propyl]-piperidinyl, 4-(4-tert-butylphenyl)-piperidinyl, 4-(4-tert-butylbenzyl)-piperidinyl, 3-(1,3,3-trimethylbutyl)-piperidinyl, 2-methyl-5-(1,5-dimethylhexyl)-piperidinyl, 4-(4-tert-butylphenyl)-piperid-3-enyl, 3-(1,5-dimethylhexyl)-pyrrolidinyl, 4-(3,3-dimethylbutyl)-piperid-3-enyl, 4-(3,3-dimethylbutyl)-piperidinyl, 4-tert-butylpiperidinyl and 3-(4-tert-butylphenyl)-pyrrolidinyl.

The novel N-substituted 2-aminodecalins and their phytophysiologically tolerated salts contain chiral centers. They are generally obtained as racemates or as diastereomer mixtures.

In the case of some of the novel compounds, pure diastereomeric compounds can be isolated, for example, by distillation or column chromatography or on the basis of solubility differences. Pure enantiomeric compounds can be obtained, for example, by resolution of the racemate with a chiral auxiliary reagent by known methods, for example via diastereomeric salts. Regarding the use of the novel 2-aminodecalin derivatives and their phytophysiologically tolerated salts as fungicides, both the diastereomers and the enantiomers and their stereoisomer mixtures obtained in the synthesis are suitable. The present invention relates to all of these compounds.

In certain cases, the 2-aminotrans-decalin derivative of the formula II can be selectively prepared or isolated.

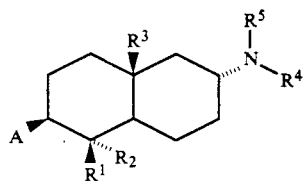

Compounds from this diastereomer series are particularly preferred.

The novel compounds can be used as fungicides.

The invention also relates to processes for the preparation of the novel N-alkylated 2-aminodecalins.

The 2-aminodecalin derivatives can be obtained, for example, from primary amines of the formula III, for example by stepwise alkylation in a conventional manner.

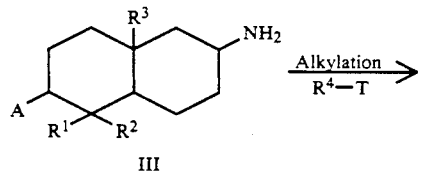

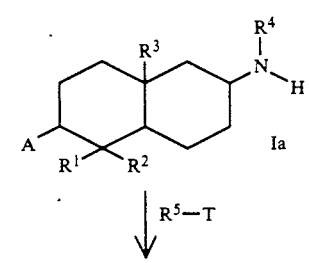

-continued

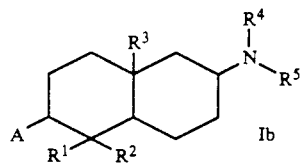

Examples of suitable alkylating agents are compounds of the type $R^4$-T and $R^5$-T, where T is an electron-attracting leaving group. Instead of the compounds of the above type, in some cases it is also possible to use aldehydes or ketones, which are then of the general formulae

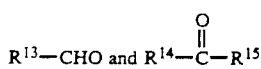

where $R^{13}$, $R^{14}$ and $R^{15}$ correspond to the radicals $R^4$ and $R^5$, with the proviso that they have one carbon atom less than $R^4$ and $R^5$.

The aldehydes or ketones are reacted with the corresponding primary or secondary amines, for example, in the presence of a reducing agent and in the presence or absence of a catalyst and of a solvent.

In another possible method for the preparation of the novel compounds, for example, a β-decalone derivative of the formula IV is aminated, either in a single-stage process or via the imine/iminium salt stage V with the use of a reducing agent and in the presence or absence of a diluent, with a correspondingly substituted amine of the formula VI

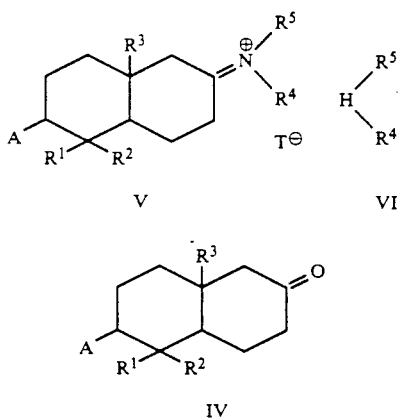

where A and $R^1$–$R^5$ have the same meaning as in I and T$^-$ is any anion.

The compounds of the formula $R^4$-T and $R^5$-T which are required as starting materials and in which T is chlorine, bromine or iodine or unsubstituted or substituted alkyl- or arylsulfonyloxy, in particular methanesulfonyloxy, trifluoromethanesulfonyloxy or p-toluenesulfonyloxy, are known and many are commercial compounds, or they can be prepared from the corresponding alcohols in a known manner.

Suitable diluents for carrying out the alkylation with compounds of type $R^4$-T and $R^5$-T are both protic and aprotic solvents.

These include, in particular, alcohols, such as methanol, ethanol, propanol, butanol and amyl alcohol, aliphatic or aromatic hydrocarbons and halohydrocarbons, for example gasoline, benzene, toluene, xylene, chlorobenzene, petroleum ether, hexane, cyclohexane, dichloromethane, chloroform and carbon tetrachloride, ethers, such as diethyl ether, dioxane, tetrahydrofuran, ethylene glycol dimethyl ether and ethylene glycol diethyl ether, ketones, such as acetone or butanone, nitriles, such as acetonitrile or propionitrile, amides, such as dimethylformamide, dimethylacetamide, N-methylformamilide, N-methylpyrrolidone or hexamethylphosphorotriamide, esters, such as ethyl acetate, and sulfoxides, such as dimethyl sulfoxide. However, diluents may also be omitted.

The novel process takes place in the presence of an acid acceptor, an inorganic or organic base. These include, for example, alkali metal hydroxides, such as sodium hydroxide, potassium hydroxide, alkali metal carbonates, such as sodium carbonate, and tertiary amines, such as trimethylamine, N,N-dimethylaniline, pyridine, N,N-dimethylaminopyridine and diazabicycloundecane (DBU).

An appropriate excess of the reacting amine may also be used as the acid acceptor and, if the amine is in liquid form, also as a diluent.

The reaction conditions for such alkylations are the relevant conventional ones and are described in, for example, Methoden d. org. Chemie (Houben-Weyl), Vol. 11/1.

The same also applies when aldehydes or ketones are used as starting materials for carrying out the novel process; these too are generally known compounds and many are commercially available.

The decalylimines or iminium salts V required for carrying out the last-mentioned process variant can be prepared from β-decalones and amines by known methods (cf. Methoden der org. Chemie (Houben-Weyl), Vol. VIII, page 1945 et seq., 4th edition, G. Thieme Verlag 1952; Methoden der org. Chemie (Houben-Weyl), Vol. XI/2, page 77 et seq., 4th edition, G. Thieme Verlag Stuttgart 1958; Methoden der Org. Chemie (Houben-Weyl), Vol. VII 2b, page 1948 et seq., 4th edition, G. Thieme Verlag Stuttgart 1976).

Complex hydrides, preferably sodium borohydride or sodium cyanoborohydride, are used as reducing agents for carrying out the novel process, and preferably alcohols, such as methanol or ethanol, are used as diluents.

The use of the mixture sodium borohydride/zinc(II) chloride has proven very particularly advantageous (S. Kimet et al., J. Org. Chem. 50 (1985), 1927).

Compounds V can, for example, also be conveniently converted with hydrogen in the presence of a catalyst or with formic acid as a reducing agent, by the Leuckart-Wallach method, into the desired 2-aminodecalins I/II.

Some of the 2-aminodecalins and β-decalones of the formulae III and IV which are required for the preparation of the novel compounds are commercially available and some are known from the literature.

The preparation of further starting compounds III and IV is outlined in scheme 1. In principle, further compounds can be prepared by these routes.

5,051,409
Scheme 1
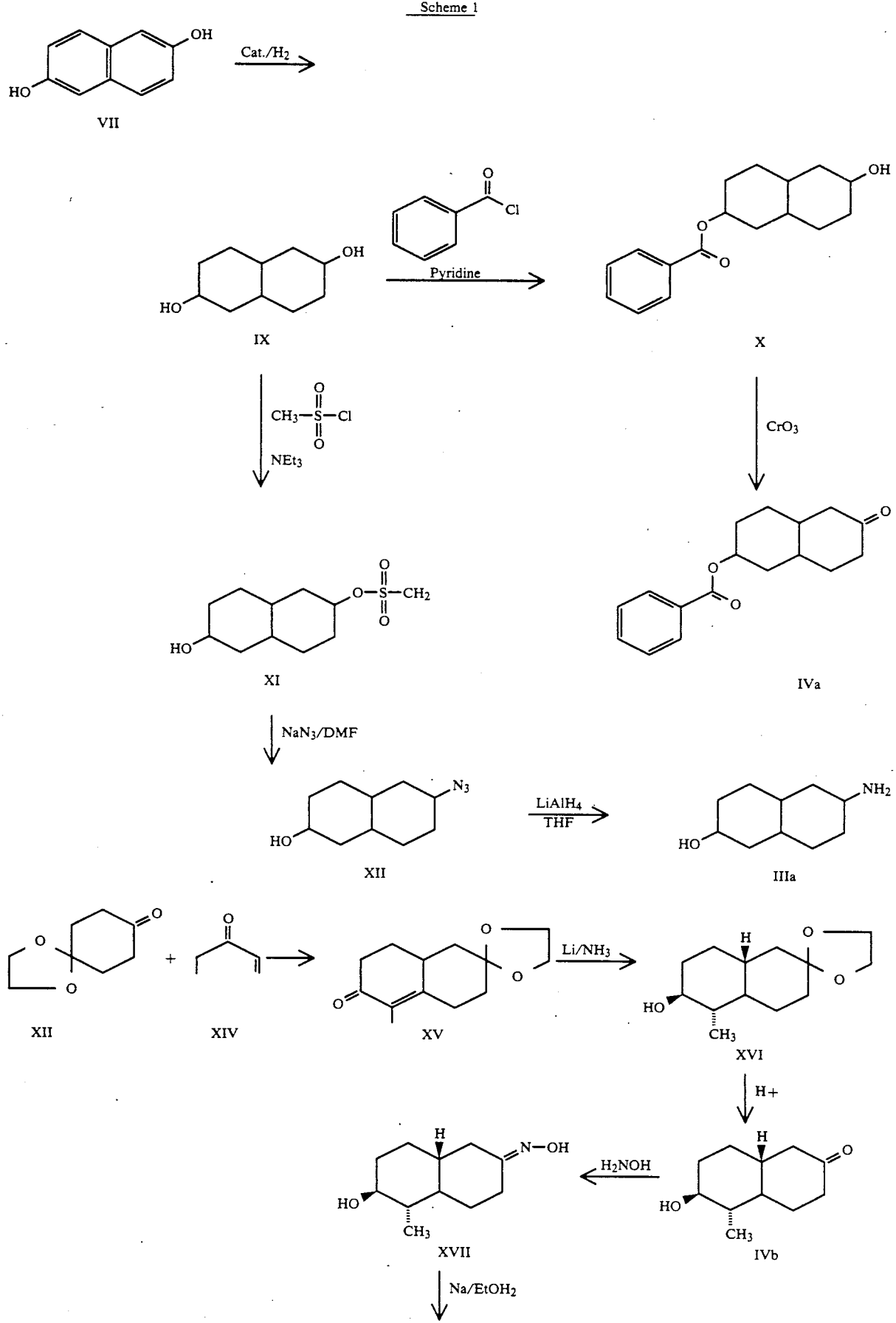

-continued
Scheme 1

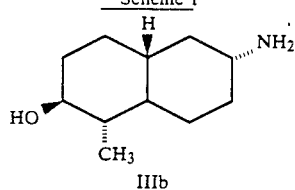
IIIb

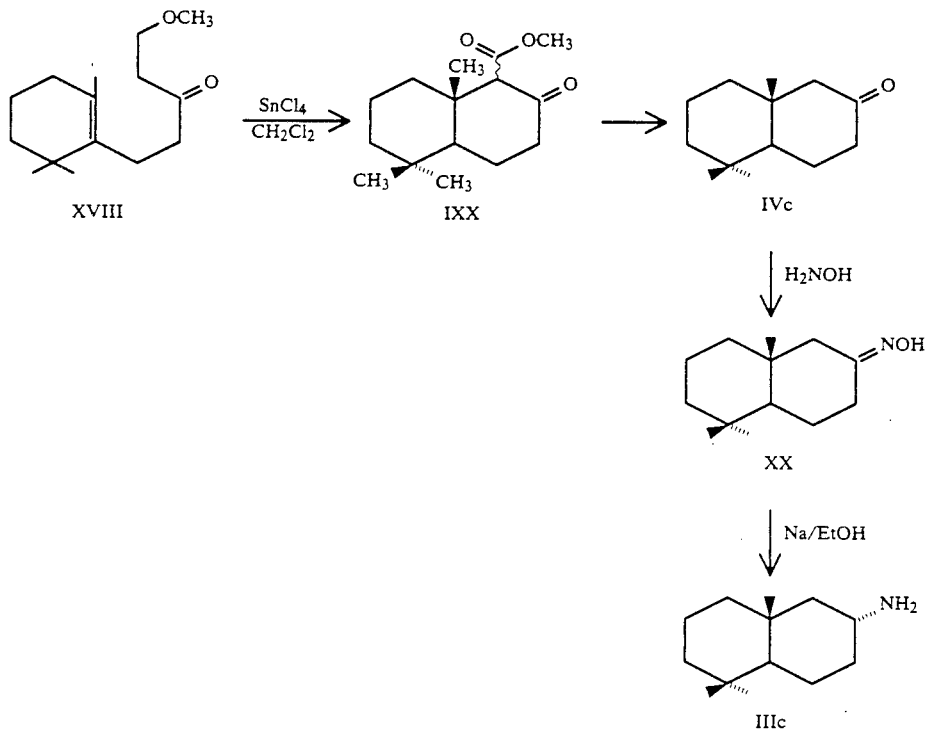

Decalindiol IX is known (R. A. Wiley et al., J. Med. Chem. 1972, 374) and can either be oxidized to the ketone IVa in a conventional manner with chromium trioxide after monobenzoylation (with benzoyl chloride/pyridine), or converted into the amine IIIa after conversion into the monomesylate, subsequent nucleophilic substitution by sodium azide (cf. for example J. A. Durden et al., J. Chem. Eng. Data 1964 (9), 228) and reduction, for example with lithium aluminum hydride (cf. for example J. H. Boyer et. al., Chem. Rev. 1954 (54), 1).

The octalone dione monoethylene ketal XV is obtainable from cyclohexanedione monoethylene ketal XIII and ethyl vinyl ketone XIV or a suitable ethylene vinyl ketone equivalent by a Robinson condensation reaction (cf. for example G. Majetich, J. Org. Chem. 42 (1977), 2327; D. Caine, J. Org. Chem. 45 (1980), 3278; S. K. Maji, J. Chem. Soc. Perk. 1, 1980, 2511, and R. B. Miller, J. Amer. Chem. Soc. 1974, 8102).

Reduction of the α,β-unsaturated carbonyl function with lithium in liquid ammonia, cleavage of the ketal with H2SO4/silica gel to form IVb, conversion of IVb into the oxime and subsequent reduction with sodium in ethanol give 6-amino-1-methyl-2-hydroxy-trans-decalin IIIb.

Hydrolysis and simultaneous decarboxylation of XIX (known from the literature: J. D. White et al., J. Org. Chem. 50 (1985), 1939) with potassium hydroxide in ethanol/water gives the trimethyl-trans-decalone IVc, which has been described earlier (G. Ohloff et al., Helv. Chim. Acta 56 (1973), 1914) and which can be converted into the decalin derivative IIIc having an equatorial amino function in a conventional manner via the oxime and subsequent reduction of the latter with sodium in ethanol.

The Examples which follow illustrate the preparation of the novel compounds.

PREPARATION EXAMPLES

Preparation of the starting compounds

Method 1: 6-Benzoyloxydecal-2-one (compound IVa)

A solution of 27.4 g (0.1 mole) of 2-benzoyloxy-6-hydroxydecalin (X) in 100 ml of dichloromethane was added dropwise, while cooling, to a mixture of 30 g (0.3 mole) of chromium trioxide and 48 g (0.6 mole) of pyridine in 150 ml of dichloromethane, and the mixture was stirred for 2 hours at room temperature (20° C.). The supernatant liquid was decanted, and the remaining residue was extracted several times with methyl tert-butyl ether. The combined organic phases were washed with dilute hydrochloric acid, sodium bicarbonate solution and sodium chloride solution, dried over sodium sulfate and evaporated down under reduced pressure. Further purification was carried out by chromatography over silica gel (CH2Cl2/diethyl ether).

A colorless oil was obtained.

IR (film): 2929, 1713, 1451, 1315, 1277, 1114, 715 cm$^{-1}$.

Method 2:2-Methylsulfonyl-6-hydroxydecaline (compound XI)

25.5 g (0.22 mole) of methanesulfonyl chloride were added dropwise, at 0°–5° C., to an initially taken mixture of 34 g (0.2 mole) of decalindiol and 30.3 g (0.3 mole) of triethylamine in 500 ml of dichloromethane. Stirring was then carried out for a further hour at room temperature. The mixture was poured onto ice, the organic phase was separated off and the aqueous phase was extracted several times with dichloromethane. The combined organic phases were washed with dilute hydrochloric acid, water and 5% strength sodium bicarbonate solution, dried over sodium sulfate and evaporated down under reduced pressure.

45.2 g (91%) of a yellow, viscous oil were obtained.
$^1$H-NMR (CDCl$_3$): $\delta = 5.0–4.5$ (m, 1H),
4.1–4.0 (m, 0.25H), H$_{eq}$), 3.65–3.5 (m, 0.75H, H$_{ax}$),
3.05–3.0 (several S, 3H), 2.1–1.4 (m, 14H).

Method 3:2-Azido-6-hydroxydecalin (compound XII)

24.8 g (0.1 mole) of decalindiol monomesylate (XI) in 1 l of dimethylformamide were heated together with 65 g (1 mole) of sodium azide and 100 ml of water for 5 hours at 90°–100° C. After cooling, the mixture was poured into 2 l of water and extracted with methyl tert-butyl ether, and the organic extracts were washed with sodium chloride solution, dried over Na$_2$SO$_4$ and evaporated down under reduced pressure.

17 g (88%) of a yellowish oil were obtained, the said oil being directly reacted further.

Method 4:2-Amino-6-hydroxydecalin (compound IIIa)

A solution of 17 g (0.09 mole) of 2-azido-6-hydroxydecalin (XII) in 100 ml of absolute tetrahydrofuran was added dropwise, at 40°–50° C., to a suspension of 3.8 g (0.1 mole) of lithium aluminum hydride in 100 ml of absolute tetrahydrofuran. The mixture was then refluxed for 3 hours. Hydrolysis was carried out with dilute sodium hydroxide solution (20 ml), sodium sulfate was added and the mixture was filtered under suction. The filtrate was evaporated down under reduced pressure. The residue was purified via the hydrochloride.

6 g (40% of theory) of IIIa were obtained as a colorless oil.
$^1$H-NMR (CDCl$_3$): $\delta = 4.1–3.4$ (m, 1H), 3.2–2.6 (m, 1H), 2.4–0.9 (m, 17H).
IR (film): 3344, 3279, 2920, 2856, 1596, 1444, 1054, 1014 cm$^{-1}$.

Method 5:1-Methyl-6,6-ethylenedioxy-Δ8a-decal-2-one (compound XV)

78 g (0.5 mole) of 4,4-ethylenedioxycyclohexanone (XIII) in 150 ml of diethyl ether were added dropwise to a solution of 22.5 g of potassium hydroxide in 150 ml of absolute ethanol and 150 ml of diethyl ether under nitrogen at 0°–5° C. After 45 minutes, 42 g (0.5 mole) of ethyl vinyl ketone in 250 ml of diethyl ether were added at 0°–5° C. in the course of 60 minutes. Stirring was carried out for 3 hours at 20° C., the mixture was poured onto ice, the organic phase was separated off and the aqueous phase was extracted with methyl tert-butyl ether. The combined organic phases were washed with water, dried, evaporated down under reduced pressure and distilled (bp. 121°–124° C./0.3 mbar).

Yield:23 g (26%) of a yellow oil.
$^1$H-NMR (CDCl$_3$): $\delta = 4.0$ (s, 4H), 2.9–1.0 (m, 11H), 1.8 (s, 3H).

IR (film): 2948, 2884, 1666, 1369, 1135, 1065 cm$^{-1}$.

Method 6:1-Methyl-2-hydroxy-6,6-ethylenedioxydecalin (compound XVI)

26 g (0.12 mole) of the product from Example 5 in 2 l of liquid ammonia, 250 ml of tetrahydrofuran and 26 g (0.35 mole) of tert-butanol were initially taken. 19.7 g (2.1 moles) of lithium wire were added in the course of 2 hours. After a further 15 minutes, 250 ml of ethanol were added dropwise in the course of 2 hours; 200 g of solid ammonium chloride were carefully added, and the ammonia was allowed to evaporate off overnight. The residue was dissolved in methyl tert-butyl ether/water and saturated with ammonium chloride. The organic phase was separated off and the aqueous phase was extracted with methyl tert-butyl ether. Working up the organic extracts in a conventional manner gave 23.4 g (86%) of a pale brown solid of melting point 56°–68° C.

$^1$H-NMR (CDCl$_3$): $\delta = 3.92$ (s, 4H), 3.2–3.05 (m, 1H), 1.05 (s, 3H), 2.1–0.6 (m, 13H).
IR (film): 3388, 2967, 2931, 2866, 1366, 1141, 1096, 1039 cm$^{-1}$.

Method 7:6-Hydroxy-5-methyl-decal-2-one (compound IVb)

19.4 g (86 millimoles) of the acetal XVI from Example 6 in 150 ml of dichloromethane was stirred with 40 ml of 15% strength sulfuric acid and 20 g of silica gel for 7 hours at 20° C. The mixture was filtered off under suction from the silica gel and washed very thoroughly with dichloromethane. The organic phase of the filtrate was separated off, washed with 5% strength sodium bicarbonate solution, dried over sodium sulfate and evaporated down under reduced pressure. 19.6 g (93%) of a yellow oil were obtained.

$^1$H-NMR (CDCl$_3$): $\delta = 3.25–3.15$ (m, 1H), 2.45–1.0 (m, 13H), 1.1 (d, 3H).

Method 8: Trans-5,5,8a-trimethyldecal-2-one (compound IVc)

A mixture of 100 g (0.4 mole) of 1-carboxymethyl-5,5,8a -trimethyldecal-2-one (compound IXX), 64 g (1.6 moles) of sodium hydroxide, 900 ml of water and 900 ml of ethanol was refluxed for 6 hours. After cooling, the mixture was acidified with dilute hydrochloric acid, extracted with dichloromethane and worked up further in a conventional manner. 76 g (98%) of a colorless oil (99% of product according to gas chromatography) were obtained.

$^1$H-NMR (CDCl$_3$): $\delta = 2.5–1.2$ (m, 13H), 1.0 (s, 3H), 0.94 (s, 3H), 0.88 (s, 3H).
IR (film): 2957, 2921, 2944, 2843, 1712, 1963 cm$^{-1}$.

Method 9: Trans-5,5,8a-trimethyldecalone oxime (compound XX)

40 g (0.2 mole) of ketone IVc from Example 8, 20.8 moles of hydroxylamine hydrochloride and 16.4 g (0.2 mole) of sodium acetate in 100 ml of water and 280 ml of ethanol were refluxed for 5 hours. The mixture was poured onto ice, the organic phase was separated off and the aqueous phase was extracted thoroughly with methyl tert-butyl ether. Further working up of the organic phases gave 34 g (81%) of a solid of melting point 120°–128° C.

IR (KBr): 3296, 2960, 2931, 2867, 1457, 1444, 921, 912 cm$^{-1}$.

The trans-6-hydroxy-5-methyldecal-2-one oxime XVII can also be prepared in a similar manner, the yield being 54% and the melting point 180° C.

$^1$H-NNR ([d$_6$]-DMSO): δ=10.1 (s, 1H), 4.5 (br.s, 1H), 3.5–0.9 (m, 13H), 0.9 (d, 3H).

Method 10: Trans-2-amino-5,5,8a-trimethyldecalin (compound IIIc)

60 g (2.6 moles) of sodium were added a little at a time, at the reflux temperature, to a solution of 20 g (95.7 millimoles) of the oxime XX from Example 9 in 360 ml of ethanol under nitrogen. Heating was continued until all of the sodium had gone into solution. After the mixture had cooled, hydrolysis was carried out carefully with water and extraction was effected with methyl tert-butyl ether. Working up the organic extracts in a conventional manner gave 30 g (80%) of a colorless oil which, according to gas chromatography and $^1$H-NMR, contained 91% of the isomer having an equatorial NH$_2$ group.

$^1$H-NMR (CDCl$_3$): δ=2.94–2.80 (m, 1H), 2.05–0.75 (m, 13H), 1.00 (s, 3H), 0.85 (s, 3H), 0.79 (s, 3H).

IR (film): 2925, 1583, 1460, 1388, 1980, 1342 cm$^{-1}$.

Trans-2-amino-6-hydroxy-5-methyldecalin (IIIb) can also be prepared in a similar manner (52% yield: mp.: 125° C.).

$^1$H-NMR (CDCl$_3$): δ=3.2–3.0 (m, 1H), 2.7–2.5 (m, 1H), 2.1–0.5 (m, 16H).

PREPARATION OF THE END PRODUCTS

Example 1

N-3,7-Dimethyloctyl-2-aminodecalin (compound No. 17)

A mixture of 5 g (35 millimoles) of 2-aminodecalin, 7.7 g (35 millimoles) of 3,7-dimethyloctyl bromide and 4.8 g (35 millimoles) of potassium carbonate in 100 ml of acetonitrile was refluxed for 8 hours. The solvent was distilled off under reduced pressure, the residue was taken up in dichloromethane/dilute sodium hydroxide solution, and the organic phase was separated off, worked up in a conventional manner and chromatographed over silica gel using hexane/methyl tert-butyl ether (for physical data, see Table).

Example 2

N-(4-Tert-butoxycyclohexylmethyl)-5,5,8a-trimethyl-2-amino-trans-decalin (compound No. 285)

2 g (10.3 millimoles) of trans-5,5,8a-trimethyl-2-aminodecalin (IIIc), 1.84 g (10.3 millimoles) of 4-tert-butoxy-1-formylcyclohexane (isomer mixture) and 5 g of a molecular sieve (4 A) in 100 ml of absolute methanol were stirred overnight at 20° C. Thereafter, 0.8 g (20.6 millimoles) of sodium borohydride were added and stirring was carried out for a further 3 hours at 40° C.

The mixture was evaporated down under reduced pressure and the residue was hydrolyzed with water and extracted with methyl tert-butyl ether. Working up in a conventional manner gave 1.65 g (44%) of a colorless oil. For physical data, see Table 2.

Example 3

N-(4-Tert-butoxybenzyl)-N-methyl-5,5,8a-trimethyl-2-amino-trans-decalin (compound No. 244)

A mixture of 2.5 g (7 millimoles) of N-(4-tert-butoxybenzyl)-5,5,8a-trimethyl-2-amino-trans-decalin (compound No. 243 from Table 2), 5.7 g of 35% strength formaldehyde solution and 2.6 g (70 millimoles) of sodium borohydride in 100 ml of methanol was stirred for 3 hours at 40° C. The mixture was evaporated down under reduced pressure, hydrolyzed with water and extracted with methyl tert-butyl ether. Working up the organic extract in a conventional manner gave 1.4 g (56%) of a yellow oil (58% according to gas chromatography). For physical data, see Table 2.

Example 4

2-(4-Tert-butylpiperidyl)-decalin (compound No. 129)

13.8 g (0.1 mole) of 4-tert-butylpiperidine, 7.5 g (0.05 mole) of β-decalin, 6.9 g (0.05 mole) of zinc (II) chloride and 6.8 g (0.11 mole) of sodium cyanoborohydride in 100 ml of methanol were stirred for 48 hours at 20° C.

The mixture was evaporated down under reduced pressure, hydrolyzed with dilute NaOH, extracted with methyl tert-butyl ether and worked up in a conventional manner.

Distillation under reduced pressure (130° C./0.2 mbar) gave 2.4 g (17.6%) of a colorless oil.

The compounds listed in Tables 1 and 2 are obtainable in the manner described in Examples 1 to 4.

TABLE 1

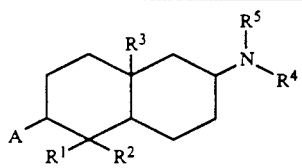

I

| Comp. No. | A | R$^1$ | R$^2$ | R$^3$ | R$^4$ | R$^5$ | Physical data: m.p, b.p. (°C.); IR(cm$^{-1}$) |
|---|---|---|---|---|---|---|---|
| 1 | H | H | H | H | H | n-hexyl | |
| 2 | H | H | H | H | H | n-heptyl | |
| 3 | H | H | H | H | H | n-octyl | |
| 4 | H | H | H | H | H | n-decyl | |
| 5 | H | H | H | H | H | n-dodecyl | |
| 6 | H | H | H | H | CH$_3$ | n-hexyl | |
| 7 | H | H | H | H | CH$_3$ | n-heptyl | |
| 8 | H | H | H | H | CH$_3$ | n-octyl | |
| 9 | H | H | H | H | CH$_3$ | n-decyl | |
| 10 | H | H | H | H | CH$_3$ | n-dodecyl | |
| 11 | H | H | H | H | H | 3-methyl-5,5-dimethyl-hexyl | |

TABLE 1-continued

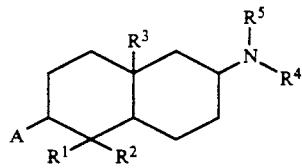

| Comp. No. | A | $R^1$ | $R^2$ | $R^3$ | $R^4$ | $R^5$ | Physical data: m.p, b.p. (°C.); IR(cm$^{-1}$) |
|---|---|---|---|---|---|---|---|
| 12 | H | H | H | H | CH$_3$ | 3-methyl-5,5-dimethyl-hexyl | |
| 13 | H | H | H | H | C$_2$H$_5$ | 3-methyl-5,5-dimethyl-hexyl | |
| 14 | H | H | H | H | H | 3-methyl-7-methyl-hept-5-enyl | 148/0.3 mbar |
| 15 | H | H | H | H | CH$_3$ | 3-methyl-7-methyl-hept-5-enyl | |
| 16 | H | H | H | H | C$_2$H$_5$ | 3-methyl-7-methyl-hept-5-enyl | |
| 17 | H | H | H | H | H | 3-methyl-7-methyl-heptyl | 145/0.2 mbar |
| 18 | H | H | H | H | CH$_3$ | 3-methyl-7-methyl-hept-5-enyl | |
| 19 | H | H | H | H | C$_2$H$_5$ | 3-methyl-7-methyl-hept-5-enyl | |
| 20 | H | H | H | H | H | 1,5,9-trimethyl-nonyl | |
| 21 | H | H | H | H | CH$_3$ | 1,5,9-trimethyl-nonyl | |
| 22 | H | H | H | H | C$_2$H$_5$ | 1,5,9-trimethyl-nonyl | |
| 23 | H | H | H | H | H | 3,5,5-trimethyl-hexyl | 140/0.2 mbar |
| 24 | H | H | H | H | CH$_3$ | 3,5,5-trimethyl-hexyl | |
| 25 | H | H | H | H | C$_2$H$_5$ | 3,5,5-trimethyl-hexyl | |
| 26 | H | H | H | H | H | 2,3,5,5-tetramethyl-hexyl | |
| 27 | H | H | H | H | CH$_3$ | 2,3,5,5-tetramethyl-hexyl | |
| 28 | H | H | H | H | H | 2,4,5,7,7-pentamethyl-octyl | |
| 29 | H | H | H | H | CH$_3$ | 2,4,5,7,7-pentamethyl-octyl | |
| 30 | H | H | H | H | H | 1,4-dimethyl-heptyl | 130/0.2 mbar |
| 31 | H | H | H | H | CH$_3$ | 1,4-dimethyl-heptyl | |
| 32 | H | H | H | H | H | tridecyl (isomer mixture) | |
| 33 | H | H | H | H | CH$_3$ | tridecyl (isomer mixture) | |
| 34 | H | H | H | H | C$_2$H$_5$ | tridecyl (isomer mixture) | |
| 35 | H | H | H | H | H | p-tert.butyl-phenyl | |
| 36 | H | H | H | H | CH$_3$ | p-tert.butyl-phenyl | |
| 37 | H | H | H | H | C$_2$H$_5$ | p-tert.butyl-phenyl | |
| 38 | H | H | H | H | H | 4,4-dimethyl-5-oxa-hexyl | |
| 39 | H | H | H | H | CH$_3$ | 4,4-dimethyl-5-oxa-hexyl | |
| 40 | H | H | H | H | H | 4,4-dimethyl-5-oxa-hexyl | |
| 41 | H | H | H | H | H | 4,4-dimethyl-5-oxa-hex-2-inyl | |
| 42 | H | H | H | H | CH$_3$ | 4,4-dimethyl-5-oxa-hex-2-inyl | |
| 43 | H | H | H | H | H | 2,4,4-trimethyl-3-oxa-pentyl | |
| 44 | H | H | H | H | CH$_3$ | 2,5,5-trimethyl-3-oxa-hexyl | |
| 44a | H | H. | H | H | H | 2,5,5-trimethyl-3-oxa-hexyl | |
| 45 | H | H | H | H | CH$_3$ | 2,5,5-trimethyl-3-oxa-hexyl | |
| 46 | H | H | H | H | H | 2,3,5,5-tetramethyl-4-oxa-hexyl | |
| 47 | H | H | H | H | CH$_3$ | 2,3,5,5-tetramethyl-4-oxa-hexyl | |
| 48 | H | H | H | H | H | 5,5-dimethyl-4-oxa-hexyl | |
| 49 | H | H | H | H | CH$_3$ | 5,5-dimethyl-4-oxa-hexyl | |
| 50 | H | H | H | H | H | 6,6-dimethyl-5-oxa-heptyl | |
| 51 | H | H | H | H | CH$_3$ | 6,6-dimethyl-5-oxa-heptyl | |
| 52 | H | H | H | H | H | p-tert.butyl-benzyl | 160/0.15 |
| 53 | H | H | H | H | CH$_3$ | p-tert.butyl-benzyl | 2926, 2854, 2785, 1513, 1464, 1448, 1363, 1268, 1111, 546 |
| 54 | H | H | H | H | C$_2$H$_5$ | p-tert.butyl-benzyl | |
| 55 | H | H | H | H | n-C$_3$H$_7$ | p-tert.butyl-benzyl | |
| 56 | H | H | H | H | iso-C$_3$H$_7$ | p-tert.butyl-benzyl | |
| 57 | H | H | H | H | cyclopropyl | p-tert.butyl-benzyl | 155/0.2 |
| 58 | H | H | H | H | H | p-tert.butyloxy-benzyl | 2976, 2922, 2857, 1505, 1460, 1447, 1365, 1234, 1161, 898 |
| 59 | H | H | H | H | CH$_3$ | p-tert.butyloxy-benzyl | |
| 60 | H | H | H | H | C$_2$H$_5$ | p-tert.butyloxy-benzyl | |
| 61 | H | H | H | H | n-C$_3$H$_7$ | p-tert.butyloxy-benzyl | |
| 62 | H | H | H | H | iso-C$_3$H$_7$ | p-tert.butyloxy-benzyl | |
| 63 | H | H | H | H | cyclopropyl | p-tert.butyloxy-benzyl | |
| 64 | H | H | H | H | H | p-1,1-dimethylpropyl-benzyl | |
| 65 | H | H | H | H | CH$_3$ | p-1,1-dimethylpropyl-benzyl | |
| 66 | H | H | H | H | C$_2$H$_5$ | p-1,1-dimethylpropyl-benzyl | |
| 67 | H | H | H | H | H | p-1,1,2-trimethylpropyl-benzyl | |
| 68 | H | H | H | H | CH$_3$ | p-1,1,2-trimethylpropyl-benzyl | |
| 69 | H | H | H | H | H | p-1,1,3,3-tetramethylbutyl-benzyl | 2921, 2856, 1512, 1465, 1448, 1394, 1365, 1108, 1018, 819 |
| 70 | H | H | H | H | CH$_3$ | p-1,1,3,3-tetramethylbutyl-benzyl | |
| 71 | H | H | H | H | H | 3-(p-tert.butyl-phenyl)-ethyl | 2924, 2858, 1512, 1463, 1447, 1363, 1121, 1109, 833, 821 |
| 72 | H | H | H | H | CH$_3$ | 3-(p-tert.butyl-phenyl)-ethyl | |
| 73 | H | H | H | H | C$_2$H$_5$ | 3-(p-tert.butyl-phenyl)-ethyl | |
| 74 | H | H | H | H | n-C$_3$H$_7$ | 3-(p-tert.butyl-phenyl)-ethyl | 2955, 2923, 2860, 2807, 1515, 1463, 1447, 1363, 1268, 826 |
| 75 | H | H | H | H | H | 3-phenyl-propyl | 176–180/1.0 mbar |
| 76 | H | H | H | H | CH$_3$ | 3-phenyl-propyl | 176–178/0.5 mbar |

TABLE 1-continued

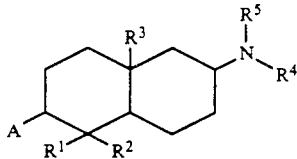

| Comp. No. | A | R¹ | R² | R³ | R⁴ | R⁵ | Physical data: m.p, b.p. (°C.); IR(cm⁻¹) |
|---|---|---|---|---|---|---|---|
| 77 | H | H | H | H | C₂H₅ | 3-phenyl-propyl | 180/2.0 mbar |
| 78 | H | H | H | H | n-C₃H₇ | 3-phenyl-propyl | 188–190/2.0 mbar |
| 79 | H | H | H | H | i-propyl | 3-phenyl-propyl | 180–183/1.0 mbar |
| 80 | H | H | H | H | H | 3-(p-tert.butyl-phenyl)-propyl | 246–250/3.0 mbar |
| 81 | H | H | H | H | CH₃ | 3-(p-tert.butyl-phenyl)-propyl | 200–204/0.8 mbar |
| 82 | H | H | H | H | C₂H₅ | 3-(p-tert.butyl-phenyl)-propyl | |
| 83 | H | H | H | H | i-propyl | 3-(p-tert.butyl-phenyl)-propyl | 210–216/1.0 mbar |
| 84 | H | H | H | H | H | 2-methyl-3-(p-tert.butyl-phenyl)-propyl | 200–220/0.5 mbar |
| 85 | H | H | H | H | CH₃ | 2-methyl-3-(p-tert.butyl-phenyl)-propyl | |
| 86 | H | H | H | H | H | 2-methyl-3-(p-tert.butyl-o-methyl-phenyl)-propyl | |
| 87 | H | H | H | H | CH₃ | 2-methyl-3-(p-tert.butyl-o-methyl-phenyl)-propyl | |
| 88 | H | H | H | H | H | p-tert.butylthio-benzyl | |
| 89 | H | H | H | H | CH₃ | p-tert.butylthio-benzyl | |
| 90 | H | H | H | H | H | p-trimethylsilyl-benzyl | |
| 91 | H | H | H | H | CH₃ | p-Trimethylsilyl-benzyl | |
| 92 | H | H | H | H | H | p-(1-methoxy-1-methyl-ethyl)-benzyl | |
| 93 | H | H | H | H | CH₃ | p-(1-methoxy-1-methyl-ethyl)-benzyl | |
| 94 | H | H | H | H | H | 2-(p-tert.butyloxy-phenyl)-ethyl | 2976, 2922, 2854, 1506, 1447, 1365, 1235, 1173, 1162, 898 |
| 95 | H | H | H | H | CH₃ | 2-(p-tert.butyloxy-phenyl)-ethyl | |
| 96 | H | H | H | H | C₂H₅ | 2-(p-tert.butyloxy-phenyl)-ethyl | |
| 97 | H | H | H | H | n-C₃H₇ | 2-(p-tert.butyloxy-phenyl)-ethyl | 2975, 2924, 2856, 1506, 1447, 1365, 1234 1174, 1162, 898 |
| 98 | H | H | H | H | H | p-tert.butyl-cyclohexyl-methyl | 2919, 2854, 1466, 1448, 1393, 1364, 1235, 1120, 897, 737 |
| 99 | H | H | H | H | CH₃ | p-tert.butyl-cyclohexyl-methyl | |
| 100 | H | H | H | H | H | p-tert.butyloxy-cyclohexyl-methyl | |
| 101 | H | H | H | H | CH₃ | p-tert.butyloxy-cyclohexyl-methyl | |
| 102 | H | H | H | H | H | 2-(p-tert.butyl-cyclohexyl)-ethyl | |
| 103 | H | H | H | H | CH₃ | 2-(p-tert.butyl-cyclohexyl)-ethyl | |
| 104 | H | H | H | H | H | 3-(p-tert.butyl-cyclohexyl)-propyl | |
| 105 | H | H | H | H | CH₃ | 3-(p-tert.butyl-cyclohexyl)-propyl | |
| 106 | H | H | H | H | H | 2-methyl-3-(p-tert.butyl-cyclohexyl)-propyl | 204–208/1.0 mbar |
| 107 | H | H | H | H | CH₃ | 2-methyl-3-(p-tert.butyl-cyclohexyl)-propyl | |
| 108 | H | H | H | H | H | 3-tert.butyl-isoxazol-5-methyl | 2922, 2857, 2963, 1464, 1448, 1366, 1606, 800, 1410, 1218 cm⁻¹ |
| 109 | H | H | H | H | CH₃ | 3-tert.butyl-isoxazol-5-methyl | 2923, 2858, 2962, 1464, 1448, 1365, 1604, 2791, 1208, 1408 cm⁻¹ |
| 110 | H | H | H | H | H | 3-heptyl-isoxazol-5-methyl | |
| 111 | H | H | H | H | CH₃ | 3-heptyl-isoxazol-5-methyl | |
| 112 | H | H | H | H | H | 1-tert.butyl-pyrrol-3-methyl | |
| 113 | H | H | H | H | CH₃ | 1-tert.butyl-pyrrol-3-methyl | |
| 114 | H | H | H | H | H | 1-tert.butyl-pyrazol-4-yl | |
| 115 | H | H | H | H | CH₃ | 1-tert.butyl-pyrazol-4-yl | |
| 116 | H | H | H | H | H | (4-methyl-cyclohexyl)-CH₂– | 2923, 2858, 1448, 1466, 1373, 1384, 1123, 1148, 733 cm⁻¹ |
| 117 | H | H | H | H | CH₃ | (4-methyl-cyclohexyl)-CH₂– | 2923, 2860, 1448, 1465, 2784, 1367, 1383, 1030, 1045, 1146 cm⁻¹ |
| 118 | H | H | H | H | H | (cyclohex-3-enyl)-CH₂– | 2923, 2859, 1447, 719, 707, 1464, 1336, 1117, 1149 cm⁻¹ |

TABLE 1-continued
I
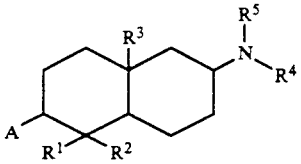
| Comp. No. | A | R¹ | R² | R³ | R⁴ | R⁵ | Physical data: m.p, b.p. (°C.); IR(cm⁻¹) |
|---|---|---|---|---|---|---|---|
| 119 | H | H | H | H | CH₃ | 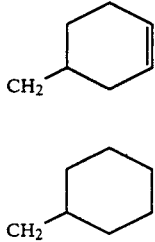 | 2923, 2860, 1447, 2779, 718, 706, 1464, 1336, 1027, 1046 cm⁻¹ |
| 120 | H | H | H | H | H | 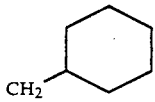 | 2922, 2860, 1463, 2447, 1365, 1381, 1117, 1148, 1060, 735 cm⁻¹ |
| 121 | H | H | H | H | CH₃ | 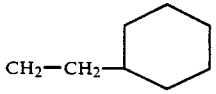 | 2924, 2862, 1448, 1461, 2780, 1365, 1048, 1381, 1024, 1122 cm⁻¹ |
| 122 | H | H | H | H | H | 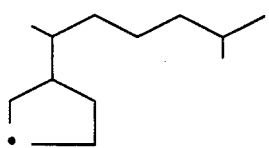 | 2919, 2858, 2980, 1465, 1447, 1366, 1382, 1148, 1117, 734 cm⁻¹ |
| 123 | H | H | H | H | | 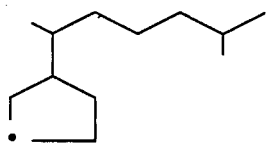 | 2924, 2860, 2978, 1465, 1947, 2787, 1366, 1382, 1026, 1047 cm⁻¹ |
| 124 | H | H | H | H | | 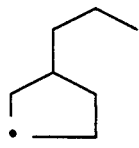 | 3289, 2923, 2855, 2783, 1466, 1447, 1377, 1366, 1150, 1058 cm⁻¹ |
| 125 | H | H | H | H | | 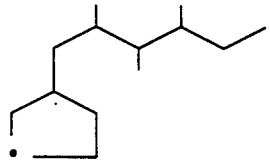 | 2923, 2863, 2777, 1718, 1476, 1465, 1376, 1364, 1161 cm⁻¹ |
| 126 | H | H | H | H | | 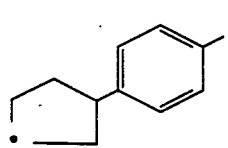 | 2924, 2863, 2777, 1718, 1476, 1465, 1392, 1376, 1152 cm⁻¹ |
| 127 | H | H | H | H | | | 2961, 2906, 2868, 2794, 1491, 1363, 1086, 1016, 830, 805 cm⁻¹ |

TABLE 1-continued
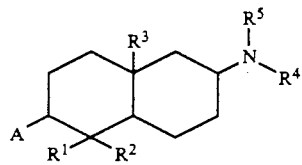
| Comp. No. | A | R¹ | R² | R³ | R⁴ | R⁵ | Physical data: m.p, b.p. (°C.); IR(cm⁻¹) |
|---|---|---|---|---|---|---|---|
| 128 | H | H | H | H | | | 2956, 2921, 2862, 2776, 1475, 1459, 1375, 1362, 829 cm⁻¹ |
| 129 | H | H | H | H | | | 130/0.2 mbar |
| 130 | H | H | H | H | | | 2973, 2851, 2795, 2742, 1463, 1446, 1378, 1362, 830, 571 cm⁻¹ |
| 131 | H | H | H | H | | | |
| 132 | H | H | H | H | | | 2920, 2854, 2793, 1460, 1447, 1379, 1361, 1270, 841, 817 |
| 133 | H | H | H | H | | | 2921, 2859, 2795, 1465, 1447, 1391, 1364, 1244, 1150, 1114 |
| 134 | H | H | H | H | | | |
| 135 | H | H | H | H | | | 110–114/0.5 mbar |
| 136 | H | H | H | H | | | 130–137/1.0 mbar |
| 137 | H | H | H | H | | | 198/0.2 mbar |

TABLE 1-continued

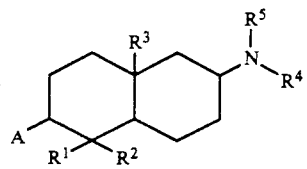
I

| Comp. No. | A | R¹ | R² | R³ | R⁴ | R⁵ | Physical data: m.p, b.p. (°C.); IR(cm⁻¹) |
|---|---|---|---|---|---|---|---|
| 138 | H | H | H | H | | (3-phenylpropyl-cyclohexyl) | 198–202/0.5 mbar |
| 139 | H | H | H | H | | (benzyl-cyclohexyl) | 174–180/0.5 mbar |
| 140 | H | H | H | H | | (3-phenylpropyl-cyclohexyl) | 206/0.5 mbar |
| 141 | H | H | H | H | | (p-methylbenzyl-cyclohexyl) | 2921, 2857, 2796, 2744, 1464, 1447, 1363, 1269, 1109, 1067180–200/1.0 mbar |
| 142 | H | H | H | H | | (sec-butyl-cyclohexyl) | 180–200/0.1 mbar |
| 143 | H | H | H | H | | (6-methylheptan-2-yl-cyclohexyl) | 2951, 2921, 2858, 1465, 1448, 1375, 1366, 1240, 1212, 1166 |
| 144 | OH | H | H | H | H | p-tert.butyl-benzyl | 2925, 2861, 1464, 1445, 1362, 1268, 1109, 1052, 831, 817 |
| 145 | OH | H | H | H | CH₃ | p-tert.butyl-benzyl | |
| 146 | OH | H | H | H | H | p-tert.butyloxy-benzyl | |
| 147 | OH | H | H | H | CH₃ | p-tert.butyloxy-benzyl | |
| 148 | OH | H | H | H | H | p-(1-methoxy-1-methyl-ethyl)-benzyl | |
| 149 | OH | H | H | H | CH₃ | p-(1-methoxy-1-methyl-ethyl)-benzyl | |
| 150 | OH | H | H | H | H | p-tert.butyl-cyclohexyl-methyl | |
| 151 | OH | H | H | H | CH₃ | p-tert.butyl-cyclohexyl-methyl | |
| 152 | OH | H | H | H | H | p-tert.butyloxy-cyclohexyl-methyl | |
| 153 | OH | H | H | H | CH₃ | p-tert.butyloxy-cyclohexyl-methyl | |
| 154 | OH | H | H | H | H | p-tert.butyl-cyclohexyl-methyl | |
| 155 | OH | H | H | H | | (6-methylheptan-2-yl-cyclopentyl) | |

TABLE 1-continued

Structure I:

Decahydronaphthalene derivative with substituents A (at position bearing R¹), R¹, R², R³, and N(R⁴)(R⁵) group.

| Comp. No. | A | R¹ | R² | R³ | R⁴ | R⁵ | Physical data: m.p, b.p. (°C.); IR(cm⁻¹) |
|---|---|---|---|---|---|---|---|
| 156 | OH | H | H | H | | 3-(p-methylphenyl)cyclopentyl (via CH₂CH₂ linker) | 3415, 2929, 2865, 1717, 1450, 1362, 1314, 1275, 1111, 712 |
| 157 | OH | H | H | H | | 3-(p-methylphenyl)cyclopentyl | |
| 158 | C₆H₅C(=O)—O | H | H | H | H | p-tert.butyl-benzyl | 2949, 2925, 2865, 1715, 1450, 1314, 1275, 1112, 1026, 712 |
| 159 | C₆H₅C(=O)—O | H | H | H | CH₃ | p-tert.butyl-benzyl | |
| 160 | C₆H₅C(=O)—O | H | H | H | H | p-tert.butyloxy-benzyl | 3017, 2962, 2922, 2860, 1513, 1461, 1452, 1362, 1113, 818 |
| 161 | C₆H₅C(=O)—O | H | H | H | CH₃ | p-tert.butyloxy-benzyl | |
| 162 | C₆H₅C(=O)—O | H | H | H | | 3-(p-methylphenyl)cyclopentyl (via CH₂CH₂ linker) | 2932, 2867, 1716, 1450, 1314, 1275, 1112, 1069, 1026, 712 |
| 163 | C₆H₅C(=O)—O | H | H | H | | 3-(2,6-dimethylheptyl)cyclopentyl | 2950, 2928, 2868, 1717, 1451, 1315, 1277, 1113, 1070, 712 |
| 164 | C₆H₅C(=O)—O | H | H | H | | 3-(p-methylphenyl)cyclopentyl | |
| 165 | H | CH₃ | CH₃ | CH₃ | | 3-(3-methylpentan-3-yl)cyclopentyl | 2949, 2866, 2844, 2775, 1715, 1461, 1388, 1382, 1216 |
| 166 | H | CH₃ | CH₃ | CH₃ | | 3-(2,6-dimethylheptyl)cyclopentyl | 3317, 2952, 2927, 2867, 2786, 1462, 1381, 1366, 1131, 1058 |

TABLE 1-continued
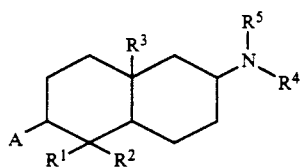
| Comp. No. | A | $R^1$ | $R^2$ | $R^3$ | $R^4$ | $R^5$ | Physical data: m.p, b.p. (°C.); IR(cm$^{-1}$) |
|---|---|---|---|---|---|---|---|
| 167 | H | CH$_3$ | CH$_3$ | CH$_3$ | | | |
| 168 | H | CH$_3$ | CH$_3$ | CH$_3$ | | | 2960, 2929, 2866, 2843, 2787, 1461, 1388, 1380, 1134 |
| 169 | H | CH$_3$ | CH$_3$ | CH$_3$ | | | |
| 170 | H | CH$_3$ | CH$_3$ | CH$_3$ | | | |
| 171 | H | CH$_3$ | CH$_3$ | CH$_3$ | | | |
| 172 | H | CH$_3$ | CH$_3$ | CH$_3$ | | | |
| 173 | H | CH$_3$ | CH$_3$ | CH$_3$ | | | |
| 174 | H | CH$_3$ | CH$_3$ | CH$_3$ | | | |
| 175 | H | CH$_3$ | CH$_3$ | CH$_3$ | | | |

TABLE 1-continued $$\text{[Structure I: decalin with } R^3 \text{ at ring junction, } A \text{ and } R^1, R^2 \text{ substituents, and } -N(R^4)(R^5) \text{ amine group]}$$ I

| Comp. No. | A | R¹ | R² | R³ | R⁴ | R⁵ | Physical data: m.p, b.p. (°C.); IR(cm⁻¹) |
|---|---|---|---|---|---|---|---|
| 176 | H | CH₃ | CH₃ | CH₃ | | cyclohexyl-CH₂– | |
| 177 | H | CH₃ | CH₃ | CH₃ | | cyclohexyl- | |
| 178 | H | CH₃ | CH₃ | CH₃ | | 3-ethylheptan-4-yl (branched alkyl) | |
| 179 | H | CH₃ | CH₃ | CH₃ | | 4-phenylheptan-4-yl | |
| 180 | H | CH₃ | CH₃ | CH₃ | | 1-phenyl-2-ethylbutyl | |
| 181 | H | CH₃ | CH₃ | CH₃ | | 1-(3-phenylpropyl)propyl | |
| 182 | H | CH₃ | CH₃ | CH₃ | | 1-(4-methylbenzyl)butyl | |
| 183 | H | CH₃ | CH₃ | CH₃ | | 1-cyclohexylpropyl (sec-butyl-cyclohexyl) | |
| 184 | H | CH₃ | CH₃ | CH₃ | | 1-(4-methylcyclohexyl)-4-methylpentyl | |

TABLE 2

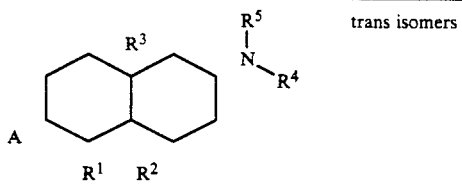

trans isomers  II

| Comp. No. | A | R¹ | R² | R³ | R⁴ | R⁵ | Physical data: m.p., b.p.(°C.); IR(cm⁻¹) |
|---|---|---|---|---|---|---|---|
| 185 | H | CH₃ | CH₃ | CH₃ | H | n-hexyl | |
| 186 | H | CH₃ | CH₃ | CH₃ | H | n-heptyl | |
| 187 | H | CH₃ | CH₃ | CH₃ | H | n-octyl | |
| 188 | H | CH₃ | CH₃ | CH₃ | H | n-decyl | |
| 189 | H | CH₃ | CH₃ | CH₃ | H | n-dodecyl | |
| 190 | H | CH₃ | CH₃ | CH₃ | CH₃ | n-hexyl | |
| 191 | H | CH₃ | CH₃ | CH₃ | CH₃ | n-heptyl | |
| 192 | H | CH₃ | CH₃ | CH₃ | CH₃ | n-octyl | |
| 193 | H | CH₃ | CH₃ | CH₃ | CH₃ | n-decyl | |
| 194 | H | CH₃ | CH₃ | CH₃ | CH₃ | n-dodecyl | |
| 195 | H | CH₃ | CH₃ | CH₃ | H | 3-methyl-5,5-dimethyl-hexyl | 2950,2906,2867,2844,1462,1388, 1379,1123,1018 |
| 196 | H | CH₃ | CH₃ | CH₃ | CH₃ | 3-methyl-5,5-dimethyl-hexyl | |
| 197 | H | CH₃ | CH₃ | CH₃ | C₂H₃ | 3-methyl-5,5-dimethyl-hexyl | |
| 198 | H | CH₃ | CH₃ | CH₃ | H | 3-methyl-7-methyl-hept-5-enyl | 2924,2866,2845,1460,1366,1204, 1124,1086,972 |
| 199 | H | CH₃ | CH₃ | CH₃ | CH₃ | 3-methyl-7-methyl-hept-5-enyl | |
| 200 | H | CH₃ | CH₃ | CH₃ | C₂H₅ | 3-methyl-7-methyl-hept-5-enyl | |
| 201 | H | CH₃ | CH₃ | CH₃ | H | 3-methyl-7-methyl-heptyl | oil |
| 202 | H | CH₃ | CH₃ | CH₃ | CH₃ | 3-methyl-7-methyl-heptyl | |
| 203 | H | CH₃ | CH₃ | CH₃ | C₂H₅ | 3-methyl-7-methyl-heptyl | |
| 204 | H | CH₃ | CH₃ | CH₃ | H | 1,5,9-trimethyl-nonyl | 3353,2954,2926,2868,2845,1462, 1378,1366,1122,1018 |
| 205 | H | CH₃ | CH₃ | CH₃ | CH₃ | 1,5,9-trimethyl-nonyl | |
| 206 | H | CH₃ | CH₃ | CH₃ | C₂H₅ | 1,5,9-trimethyl-nonyl | |
| 207 | H | CH₃ | CH₃ | CH₃ | n-C₃H₇ | 1,5,9-trimethyl-nonyl | |
| 208 | H | CH₃ | CH₃ | CH₃ | H | 3,5,5-trimethyl-hexyl | |
| 209 | H | CH₃ | CH₃ | CH₃ | CH₃ | 3,5,5-trimethyl-hexyl | |
| 210 | H | CH₃ | CH₃ | CH₃ | C₂H₅ | 3,5,5-trimethyl-hexyl | |
| 211 | H | CH₃ | CH₃ | CH₃ | H | 2,3,5,5-tetramethyl-hexyl | 2952,2931,2867,2843,1462,1388, 1379,1125 |
| 212 | H | CH₃ | CH₃ | CH₃ | CH₃ | 2,3,5,5-tetramethyl-hexyl | |
| 213 | H | CH₃ | CH₃ | CH₃ | H | 2,4,5,7,7-pentamethyl-octyl | 2951,2928,2867,2844,1666,1462, 1380,1365,1123 |
| 214 | H | CH₃ | CH₃ | CH₃ | CH₃ | 2,4,5,7,7-pentamethyl-octyl | |
| 215 | H | CH₃ | CH₃ | CH₃ | H | 1,4-dimethyl-heptyl | |
| 216 | H | CH₃ | CH₃ | CH₃ | CH₃ | 1,4-dimethyl-heptyl | |
| 217 | H | CH₃ | CH₃ | CH₃ | H | tridecyl (isomer mixture) | |
| 218 | H | CH₃ | CH₃ | CH₃ | CH₃ | tridecyl (isomer mixture) | |
| 219 | H | CH₃ | CH₃ | CH₃ | C₂H₅ | tridecyl (isomer mixture) | |
| 220 | H | CH₃ | CH₃ | CH₃ | H | p-tert.butyl-cyclohexyl | |
| 221 | H | CH₃ | CH₃ | CH₃ | CH₃ | p-tert.butyl-cyclohexyl | |
| 222 | H | CH₃ | CH₃ | CH₃ | C₂H₅ | p-tert.butyl-cyclohexyl | |
| 223 | H | CH₃ | CH₃ | CH₃ | H | 4,4-dimethyl-5-oxa-hexyl | |
| 224 | H | CH₃ | CH₃ | CH₃ | CH₃ | 4,4-dimethyl-5-oxa-hexyl | |
| 225 | H | CH₃ | CH₃ | CH₃ | H | 4,4-dimethyl-5-oxa-hex-2-ynyl | |
| 226 | H | CH₃ | CH₃ | CH₃ | CH₃ | 4,4-dimethyl-5-oxa-hex-2-ynyl | |
| 227 | H | CH₃ | CH₃ | CH₃ | H | 2,4,4-trimethyl-3-oxa-pentyl | |
| 228 | H | CH₃ | CH₃ | CH₃ | CH₃ | 2,4,4-trimethyl-3-oxa-pentyl | |
| 229 | H | CH₃ | CH₃ | CH₃ | H | 2,5,5-trimethyl-3-oxa-hexyl | |
| 230 | H | CH₃ | CH₃ | CH₃ | CH₃ | 2,5,5-trimethyl-3-oxa-hexyl | |
| 231 | H | CH₃ | CH₃ | CH₃ | H | 2,3,5,5-tetramethyl-4-oxa-hexyl | |
| 232 | H | CH₃ | CH₃ | CH₃ | CH₃ | 2,3,5,5-tetramethyl-4-oxa-hexyl | |
| 233 | H | CH₃ | CH₃ | CH₃ | H | 5,5-dimethyl-4-oxa-hexyl | |
| 234 | H | CH₃ | CH₃ | CH₃ | CH₃ | 5,5-dimethyl-4-oxa-hexyl | |
| 235 | H | CH₃ | CH₃ | CH₃ | H | 6,6-dimethyl-5-oxa-heptyl | |
| 236 | H | CH₃ | CH₃ | CH₃ | CH₃ | 6,6-dimethyl-5-oxa-heptyl | |
| 237 | H | CH₃ | CH₃ | CH₃ | H | p-tert.butyl-benzyl | 2994,2961,2948,2926,2906,2866, 1461,13860,1365 |
| 238 | H | CH₃ | CH₃ | CH₃ | CH₃ | p-tert.butyl-benzyl | |
| 239 | H | CH₃ | CH₃ | CH₃ | C₂H₅ | p-tert.butyl-benzyl | |
| 240 | H | CH₃ | CH₃ | CH₃ | n-C₃H₇ | p-tert.butyl-benzyl | |
| 241 | H | CH₃ | CH₃ | CH₃ | iso-C₃H₄ | p-tert.butyl-benzyl | |
| 242 | H | CH₃ | CH₃ | CH₃ | cyclopropyl | p-tert.butyl-benzyl | |
| 243 | H | CH₃ | CH₃ | CH₃ | H | p-tert.butyloxy-benzyl | 2975,2928,2866,2843,1506,1460, 1365,1234,1161,898 |
| 244 | H | CH₃ | CH₃ | CH₃ | CH₃ | p-tert.butyloxy-benzyl | 2974,2930,2866,2843,1504, 1365,1233,1172,1160,899 cm⁻¹ |
| 245 | H | CH₃ | CH₃ | CH₃ | C₂H₅ | p-tert.butyloxy-benzyl | |
| 246 | H | CH₃ | CH₃ | CH₃ | n-C₃H₇ | p-tert.butyloxy-benzyl | |
| 247 | H | CH₃ | CH₃ | CH₃ | allyl | p-tert.butyloxy-benzyl | oil |

TABLE 2-continued trans isomers

II $$\text{structure with A, R}^1, R^2, R^3, R^5, R^4, N$$

| Comp. No. | A | R$^1$ | R$^2$ | R$^3$ | R$^4$ | R$^5$ | Physical data: m.p., b.p.(°C.); IR(cm$^{-1}$) |
|---|---|---|---|---|---|---|---|
| 248 | H | CH$_3$ | CH$_3$ | CH$_3$ | propargyl | p-tert.butyloxy-benzyl | oil |
| 249 | H | CH$_3$ | CH$_3$ | CH$_3$ | H | p-1,1-dimethylpropyl-benzyl | 2963,2925,2878,2867,1461,1387, 1379,1124 |
| 250 | H | CH$_3$ | CH$_3$ | CH$_3$ | CH$_3$ | p-1,1-dimethylpropyl-benzyl | |
| 251 | H | CH$_3$ | CH$_3$ | CH$_3$ | C$_2$H$_5$ | p-1,1-dimethylpropyl-benzyl | |
| 252 | H | CH$_3$ | CH$_3$ | CH$_3$ | H | p-1,1,2-trimethylpropyl-benzyl | 2963,2927,2875,2843,1461,1388, 1378,1124,1110 |
| 253 | H | CH$_3$ | CH$_3$ | CH$_3$ | CH$_3$ | p-1,1,2-trimethylpropyl-benzyl | |
| 254 | H | CH$_3$ | CH$_3$ | CH$_3$ | H | p-1,1,3,3-tetramethylbutyl-benzyl | 154–70/0.3 mbar |
| 255 | H | CH$_3$ | CH$_3$ | CH$_3$ | CH$_3$ | p-1,1,3,3-tetramethylbutyl-benzyl | |
| 256 | H | CH$_3$ | CH$_3$ | CH$_3$ | H | 3-(p-tert.butyl-phenyl)-ethyl | |
| 257 | H | CH$_3$ | CH$_3$ | CH$_3$ | CH$_3$ | 3-(p-tert.butyl-phenyl)-ethyl | |
| 258 | H | CH$_3$ | CH$_3$ | CH$_3$ | C$_2$H$_5$ | 3-(p-tert.butyl-phenyl)-ethyl | |
| 259 | H | CH$_3$ | CH$_3$ | CH$_3$ | n-C$_3$H$_7$ | 3-(p-tert.butyl-phenyl)-ethyl | |
| 260 | H | CH$_3$ | CH$_3$ | CH$_3$ | H | 3-phenyl-propyl | |
| 261 | H | CH$_3$ | CH$_3$ | CH$_3$ | CH$_3$ | 3-phenyl-propyl | |
| 262 | H | CH$_3$ | CH$_3$ | CH$_3$ | C$_2$H$_5$ | 3-phenyl-propyl | |
| 263 | H | CH$_3$ | CH$_3$ | CH$_3$ | n-C$_3$H$_7$ | 3-phenyl-propyl | |
| 264 | H | CH$_3$ | CH$_3$ | CH$_3$ | i-propyl | 3-phenyl-propyl | |
| 265 | H | CH$_3$ | CH$_3$ | CH$_3$ | H | 3-(tert.butyl-phenyl)-propyl | |
| 266 | H | CH$_3$ | CH$_3$ | CH$_3$ | CH$_3$ | 3-(tert.butyl-phenyl)-propyl | |
| 267 | H | CH$_3$ | CH$_3$ | CH$_3$ | C$_2$H$_5$ | 3-(tert.butyl-phenyl)-propyl | |
| 268 | H | CH$_3$ | CH$_3$ | CH$_3$ | i-propyl | 3-(tert.butyl-phenyl)-propyl | |
| 269 | H | CH$_3$ | CH$_3$ | CH$_3$ | H | 2-methyl-3-(p-tert.butyl-phenyl)-propyl | 2994,2960,2926,2867,2843,1461 1379,1365,1124,1109 |
| 270 | H | CH$_3$ | CH$_3$ | CH$_3$ | CH$_3$ | 2-methyl-3-(p-tert.butyl-phenyl)-propyl | |
| 271 | H | CH$_3$ | CH$_3$ | CH$_3$ | H | 2-methyl-3-(p-tert.butyl-o-methyl-phenyl)-propyl | 2949,2927,2866,2843,1506,1461, 1388,1379,1362,1125 |
| 272 | H | CH$_3$ | CH$_3$ | CH$_3$ | CH$_3$ | 2-methyl-3-(p-tert.butyl-o-methyl-phenyl)-propyl | |
| 273 | H | CH$_3$ | CH$_3$ | CH$_3$ | H | p-tert.butylthio-benzyl | 2959/2922,2865,2842,1471,1457, 1380,1363,1168 |
| 274 | H | CH$_3$ | CH$_3$ | CH$_3$ | CH$_3$ | p-tert.butylthio-benzyl | |
| 275 | H | CH$_3$ | CH$_3$ | CH$_3$ | H | p-trimethylsilyl-benzyl | |
| 276 | H | CH$_3$ | CH$_3$ | CH$_3$ | CH$_3$ | p-trimethylsilyl-benzyl | |
| 277 | H | CH$_3$ | CH$_3$ | CH$_3$ | H | p-(1-methoxy-1-methyl-ethyl)-benzyl | 2973,2928,2866,2842,1461,1378, 1361,1172,1075,826 |
| 278 | H | CH$_3$ | CH$_3$ | CH$_3$ | CH$_3$ | p-(1-methoxy-1-methyl-ethyl)-benzyl | |
| 279 | H | CH$_3$ | CH$_3$ | CH$_3$ | H | p-(1-tert.butyloxy-phenyl)-ethyl | |
| 280 | H | CH$_3$ | CH$_3$ | CH$_3$ | CH$_3$ | p-(1-tert.butyloxy-phenyl)-ethyl | |
| 281 | H | CH$_3$ | CH$_3$ | CH$_3$ | C$_2$H$_5$ | p-(1-tert.butyloxy-phenyl)-ethyl | |
| 282 | H | CH$_3$ | CH$_3$ | CH$_3$ | n-C$_3$H$_7$ | p-(1-tert.butyloxy-phenyl)-ethyl | |
| 283 | H | CH$_3$ | CH$_3$ | CH$_3$ | H | p-tert.butyl-cyclohexyl-methyl | 2935,2865,2844,1466,1449,1388, 1379,1125,1047 |
| 284 | H | CH$_3$ | CH$_3$ | CH$_3$ | CH$_3$ | p-tert.butyl-cyclohexyl-methyl | |
| 285 | H | CH$_3$ | CH$_3$ | CH$_3$ | H | p-tert.butyloxy-cyclohexyl-methyl | 2967,2929,2865,2844,1461,1387, 1362,1198,1086,1066 |
| 286 | H | CH$_3$ | CH$_3$ | CH$_3$ | CH$_2$ | p-tert.butyloxy-cyclohexyl-methyl | |
| 287 | H | CH$_3$ | CH$_3$ | CH$_3$ | H | 2-(p-tert.butyl-cyclohexyl)-ethyl | |
| 288 | H | CH$_3$ | CH$_3$ | CH$_3$ | CH$_3$ | 2-(p-tert.butyl-cyclohexyl)-ethyl | |
| 289 | H | CH$_3$ | CH$_3$ | CH$_3$ | H | 3-(p-tert.butyl-cyclohexyl)-propyl | |
| 290 | H | CH$_3$ | CH$_3$ | CH$_3$ | CH$_3$ | 3-(p-tert.butyl-cyclohexyl)-propyl | |
| 291 | H | CH$_3$ | CH$_3$ | CH$_3$ | H | 2-methyl-3-(p-tert.butyl-cyclohexyl)-propyl | |
| 292 | H | CH$_3$ | CH$_3$ | CH$_3$ | CH$_3$ | 2-methyl-3-(p-tert.butyl-cyclohexyl)-propyl | |
| 293 | H | CH$_3$ | CH$_3$ | CH$_3$ | H | 3-tert.butyl-isoxazol-5-methyl | 2962,2925,2867,2844,1606,1462, 1388,1380,1126 |
| 294 | H | CH$_3$ | CH$_3$ | CH$_3$ | CH$_3$ | 3-tert.butyl-isoxazol-5-methyl | |
| 295 | H | CH$_3$ | CH$_3$ | CH$_3$ | H | 3-heptyl-isoxazol-5-methyl | 2926,2854,1606,1461,1429,1388, 1380,1133 cm$^{-1}$ |
| 296 | H | CH$_3$ | CH$_3$ | CH$_3$ | CH$_3$ | 3-heptyl-isoxazol-5-methyl | |
| 297 | H | CH$_3$ | CH$_3$ | CH$_3$ | H | 1-tert.butyl-pyrrol-3-methyl | |
| 298 | H | CH$_3$ | CH$_3$ | CH$_3$ | CH$_3$ | 1-tert.butyl-pyrrol-3-methyl | |
| 299 | H | CH$_3$ | CH$_3$ | CH$_3$ | H | 1-tert.butyl-pyrazol-4-yl | 2968,2927,2842,1961,1389,1366, 1219,1123,977 cm$^{-1}$ |
| 300 | H | CH$_3$ | CH$_3$ | CH$_3$ | CH$_3$ | 1-tert.butyl-pyrazol-4-yl | |

TABLE 2-continued $$\text{II, trans isomers}$$

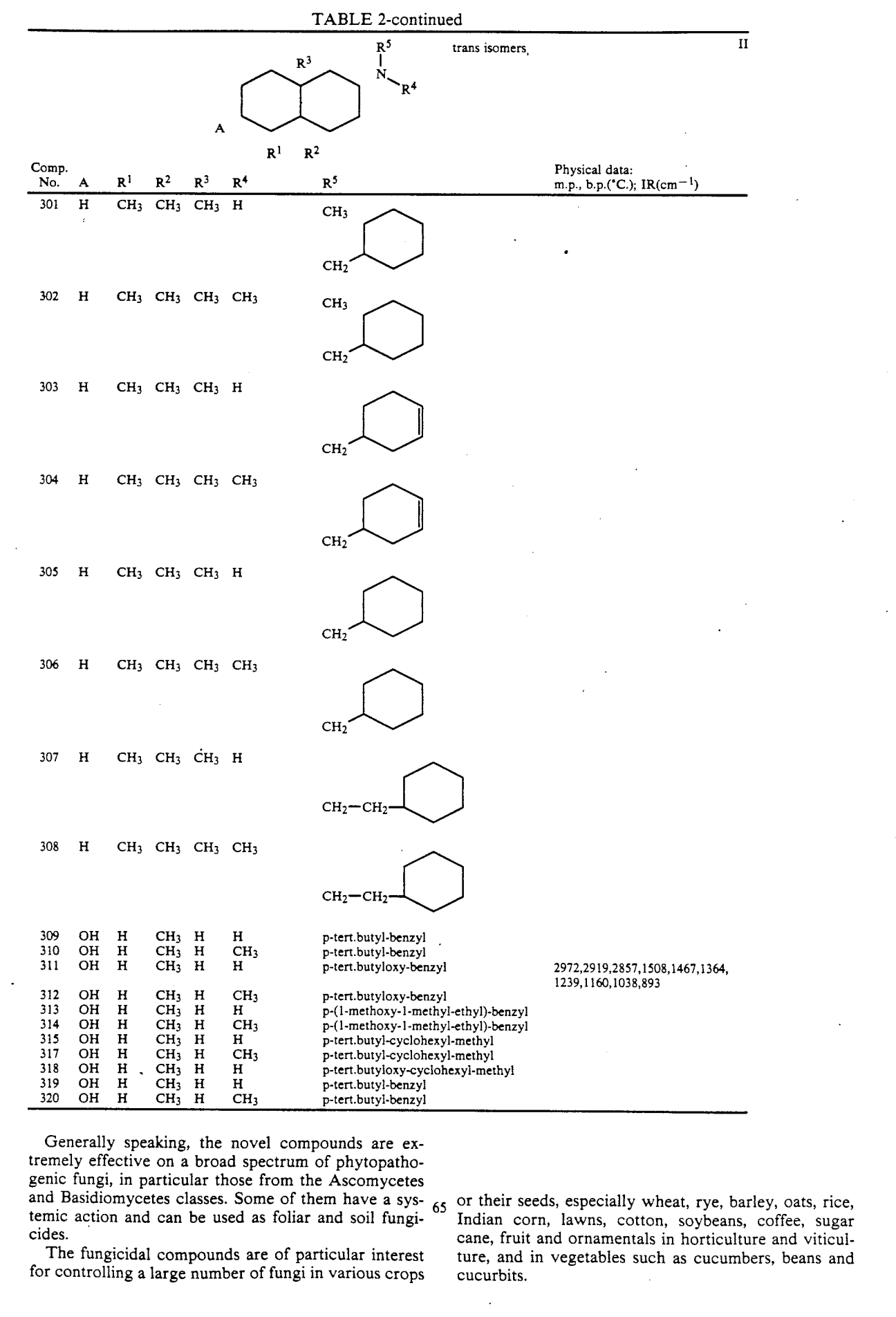

Structure II: decalin with substituents A, R¹, R² on one ring position and R³, CH(R⁴)(R⁵)... actually: decalin bearing A, R¹, R², R³ and a -N(R⁴)(R⁵) group.

| Comp. No. | A | R¹ | R² | R³ | R⁴ | R⁵ | Physical data: m.p., b.p.(°C.); IR(cm⁻¹) |
|---|---|---|---|---|---|---|---|
| 301 | H | $CH_3$ | $CH_3$ | $CH_3$ | H | $CH_3$–$CH_2$–cyclohexyl | |
| 302 | H | $CH_3$ | $CH_3$ | $CH_3$ | $CH_3$ | $CH_3$–$CH_2$–cyclohexyl | |
| 303 | H | $CH_3$ | $CH_3$ | $CH_3$ | H | $CH_2$–cyclohexenyl | |
| 304 | H | $CH_3$ | $CH_3$ | $CH_3$ | $CH_3$ | $CH_2$–cyclohexenyl | |
| 305 | H | $CH_3$ | $CH_3$ | $CH_3$ | H | $CH_2$–cyclohexyl | |
| 306 | H | $CH_3$ | $CH_3$ | $CH_3$ | $CH_3$ | $CH_2$–cyclohexyl | |
| 307 | H | $CH_3$ | $CH_3$ | $CH_3$ | H | $CH_2$–$CH_2$–cyclohexyl | |
| 308 | H | $CH_3$ | $CH_3$ | $CH_3$ | $CH_3$ | $CH_2$–$CH_2$–cyclohexyl | |
| 309 | OH | H | $CH_3$ | H | H | p-tert.butyl-benzyl | |
| 310 | OH | H | $CH_3$ | H | $CH_3$ | p-tert.butyl-benzyl | |
| 311 | OH | H | $CH_3$ | H | H | p-tert.butyloxy-benzyl | 2972,2919,2857,1508,1467,1364, 1239,1160,1038,893 |
| 312 | OH | H | $CH_3$ | H | $CH_3$ | p-tert.butyloxy-benzyl | |
| 313 | OH | H | $CH_3$ | H | H | p-(1-methoxy-1-methyl-ethyl)-benzyl | |
| 314 | OH | H | $CH_3$ | H | $CH_3$ | p-(1-methoxy-1-methyl-ethyl)-benzyl | |
| 315 | OH | H | $CH_3$ | H | H | p-tert.butyl-cyclohexyl-methyl | |
| 317 | OH | H | $CH_3$ | H | $CH_3$ | p-tert.butyl-cyclohexyl-methyl | |
| 318 | OH | H | $CH_3$ | H | H | p-tert.butyloxy-cyclohexyl-methyl | |
| 319 | OH | H | $CH_3$ | H | H | p-tert.butyl-benzyl | |
| 320 | OH | H | $CH_3$ | H | $CH_3$ | p-tert.butyl-benzyl | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 58 is mixed with 10 parts by weight of N-methyl-α-pyrrolidone. A mixture is obtained which is suitable for application in the form of very fine drops.

II. 20 parts by weight of compound no. 74 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 47 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, and aqueous dispersion is obtained.

IV. 20 parts by weight of compound no. 243 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 53 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 75 is intimately mixed with 97 parts by weight of particulate kaolin. A dust is obtained containing 3% by weight of the active ingredient.

VII. 30 parts by weight of compound no. 84 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 122 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 124 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:

sulfur, dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

Use Examples

Decal-2-yl-(2-methylprop-3-yl)-N-cis-2,6-dimethylmorpholine (A) disclosed in EP 254,150 and N,N-dimethyl-2-aminodecalin (B) disclosed in Liebigs Ann. Chemie, vol. 683, pp. 49–54 (1965) were used for comparison purposes.

Use Example 1

Action on Wheat Brown Rust

Leaves of pot-grown wheat seedlings of the "Frühgold" variety were dusted with spores of brown rust (*Puccinia recondita*). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 58, 74, 97 and 243, applied as 0.025 wt % spray liquors, had a better fungicidal action (100%) than prior art active ingredients A and B (55%).

Use Example 2

Action on *Botrytis cinerea* in Pimientos

Pimiento seedlings of the "Neusiedler Ideal Elite" variety with 4 to 5 well developed leaves were sprayed to runoff with aqueous suspensions containing (dry basis) 80% of active ingredient and 20% of emulsifier. After the sprayed-on layer had dried, the plants were sprayed with a conidial suspension of the fungus *Botrytis cinerea* and kept in a high-humidity chamber at 22° to 24° C. After 5 days, the disease had spread on the untreated control plants to such an extent that the necroses covered the major portion of the leaves.

The results show that active ingredients 53, 75, 84, 122, 124, 129, 130, 144, 158, 160, 198, 249, 252, 285 and 311, applied as 0.05% spray liquors, had a better fungicidal action (97%) than the prior art comparative agents A and B (35%).

Use Example 3

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients nos. 23, 35, 53, 71, 74, 80, 94, 97, 98, 120, 122, 123, 126, 127, 128, 129, 130, 132, 138, 139, 141, 142, 166, 198, 204, 237, 243, 252, 271, 273, 283 and 311, applied as 0.05% spray liquors, had a better fungicidal action (97%) than prior art active ingredients A and B (35%).

We claim:
1. 2-Aminodecalin derivatives of the formula I

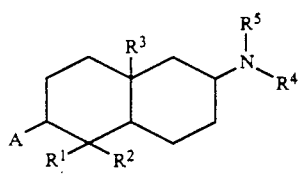

where
$R^1$, $R^2$ and $R^3$ are identical or different and are each H or methyl, A is H, OH, O-$C_1$-$C_4$-alkylcarbonyl, O-benzyl or O—$CH_3$, $R^4$ is H, $C_1$-$C_4$-alkyl, $C_2$-$C_4$-alkenyl, $C_3$-$C_4$-alkynyl or cyclopropyl, $R^5$ is $C_3$-$C_{18}$-alkyl, $C_3$-$C_{18}$-alkenyl or $C_3$-$C_{18}$-alkynyl which is unsubstituted or monosubstituted to trisubstituted by $C_1$-$C_8$-alkoxy, $C_5$-$C_{12}$-cycloalkyl or $C_5$-$C_{12}$-cycloalkenyl which is unsubstituted or monosubstituted to trisubstituted by $C_3$-$C_8$-alkyl, $C_3$-$C_8$-alkenyl or $C_3$-$C_8$-alkoxy, or $R^5$ is a radical

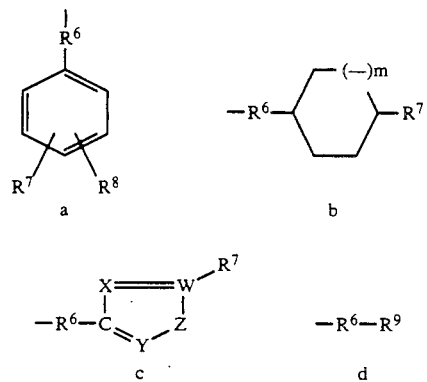

where $R^6$ is $C_1$-$C_5$-alkylene or $C_1$-$C_5$-alkenylene, $R^7$ is $C_3$-$C_8$-alkyl, $C_3$-$C_8$-alkenyl, $C_3$-$C_8$-alkoxy, $C_1$-$C_3$-alkoxy-$C_2$-$C_5$-alkyl, $C_3$-$C_5$-alkylthio or trimethylsilyl, $R^8$ is H or $CH_3$, $R^9$ is $C_6$-$C_{10}$-bicycloalkyl or $C_6$-$C_{10}$-bicycloalkenyl which is unsubstituted or substituted by 2 or 3 methyl groups, W, X, Y and Z are each a ring atom in an aromatic 5-membered heterocyclic ring, i.e., 1 or 2 radicals from the group consisting of O, S, N, NH, N—$R^7$ and 2 or 3 radicals CH and C—$R^7$, m is 0, 1 or 2, so that the radical 5b contains a cyclohexyl, cycloheptyl or cyclopentyl radical, $R^4$ and $R^5$, together with the nitrogen atom on which they are substituents, may furthermore form a 5-membered or 6-membered ring e or f

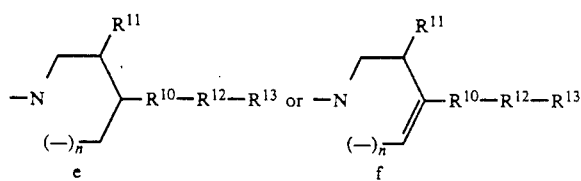

where $R^{10}$ is H or $(CH_2)_q$, in which q is 0, 1, 2, 3 or 4 or methyl, ethyl or branched $C_3$-$C_8$-alkyl, $R^{11}$ is H or $C_1$-$C_5$-alkyl, $R^{12}$ is H or phenyl when $R^{10}$ is not H, $R^{13}$ is $C_3$-$C_6$-alkyl when $R^{12}$ is phenyl, n is 0 or 1, so that the radical 5e or 5f contains a 6-membered or 5-membered heterocyclic ring, and their plant-tolerated salts and N-oxides.

2. 2-Aminodecalin derivatives of the formula II

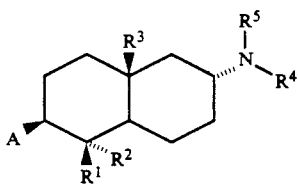

which have a trans-decalin skeleton, A and $R^3$ are in the cis position, $R^2$ and $NR^4R^5$ are in the trans position, and $R^1$ to $R^5$ and A have the same meanings as in claim 1, and their plant-tolerated salts and N-oxides.

3. A compound of the formula I as set forth in claim 1, wherein A, $R^1$, $R^2$, $R^3$ and $R^4$ are hydrogen and $R^5$ is 3,7-dimethyl-octyl.

4. A compound of the formula I as set forth in claim 1, wherein A is hydrogen, $R^1$, $R^2$, $R^3$ and $R^4$ are methyl and $R^5$ is 4-tert.butoxy-cyclohexyl-methyl.

5. A compound of the formula I as set forth in claim 1, wherein A and $R^4$ are hydrogen, $R^1$, $R^2$ and $R^3$ are methyl and $R^5$ is 4-tert.butoxy-benzyl.

6. A compound of the formula I as set forth in claim 1, wherein A, $R^1$, $R^2$ and $R^3$ are hydrogen and $R^4$ and $R^5$, together with the nitrogen atom whose substituents they are, are 4-tert.butyl-piperidinyl.

7. A fungicidal agent containing a fungicidally effective amount of a compound of the formula I

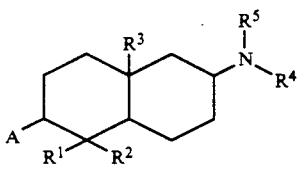

where
$R^1$, $R^2$ and $R^3$ are identical or different and are each H or methyl,
A is H, OH, O-$C_1$-$C_4$-alkylcarbonyl, O-benzoyl or O—$CH_3$,
$R^4$ is H, $C_1$-$C_4$-alkyl, $C_2$-$C_4$-alkenyl, $C_3$-$C_4$-alkynyl or cyclopropyl,
$R^5$ is $C_3$-$C_{18}$-alkyl, $C_3$-$C_{18}$-alkenyl or $C_3$-$C_{18}$-alkynyl which is unsubstituted or monosubstituted to trisubstituted by $C_1$-$C_8$-alkoxy, $C_5$-$C_{12}$-cycloalkyl or $C_5$-$C_{12}$-cycloalkenyl which is unsubstituted or monosubstituted to trisubstituted by $C_3$-$C_8$-alkyl, $C_3$-$C_8$-alkenyl or $C_3$-$C_8$-alkoxy,
or $R^5$ is a radical

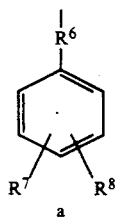 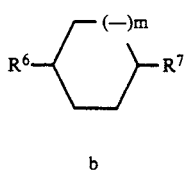

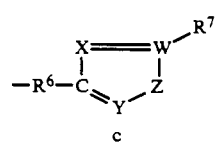 

where $R^6$ is $C_1$-$C_5$-alkylene or $C_1$-$C_5$-alkenylene,
$R^7$ is $C_3$-$C_8$-alkyl, $C_3$-$C_8$-alkenyl, $C_3$-$C_8$-alkoxy, $C_1$-$C_3$-alkoxy-$C_2$-$C_5$-alkyl, $C_3$-$C_5$-alkylthio or trimethylsilyl,
$R^8$ is H or $CH_3$,
$R^9$ is $C_6$-$C_{10}$-bicycloalkyl or $C_6$-$C_{10}$-bicycloalkenyl which is unsubstituted or substituted by 2 or 3 methyl groups,
W, X, Y and Z are each a ring atom in an aromatic 5-membered heterocyclic ring, i.e., 1 or 2 radicals from the group consisting of O, S, N, NH, N—$R^7$ and 2 or 3 radicals CH and C—$R^7$,
m is 0, 1 or 2, so that the radical 5b contains a cyclohexyl, cycloheptyl or cyclopentyl radical,
$R^4$ and $R^5$, together with the nitrogen atom on which they are substituents, may furthermore form a 5-membered or 6-membered ring e or f

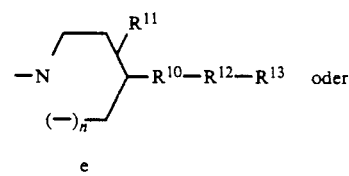

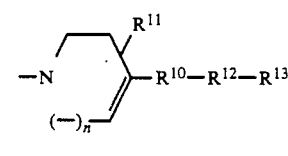

where $R^{10}$ is H or $(CH_2)_q$, in which q is 0, 1, 2, 3 or 4 or methyl, ethyl or branched $C_3$-$C_8$-alkyl,
$R^{11}$ is H or $C_1$-$C_5$-alkyl,
$R^{12}$ is H or phenyl when $R^{10}$ is not H,
$R^{13}$ is $C_3$-$C_6$-alkyl when $R^{12}$ is phenyl,
n is 0 or 1, so that the radical 5e or 5f contains a 6-membered or 5-membered heterocyclic ring,
or a plant-tolerated salt or N-oxide thereof, and a solid or liquid carrier.

8. A process for combating fungi, wherein a fungicidally effective amount of a compound of the formula I

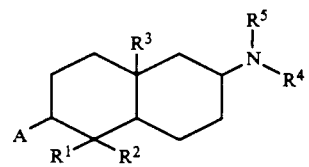

where
$R^1$, $R^2$ and $R^3$ are identical or different and are each H or methyl,
A is H, OH, O-$C_1$-$C_4$-alkylcarbonyl, O-benzoyl or O—$CH_3$,
$R^4$ is H, $C_1$-$C_4$-alkyl, $C_2$-$C_4$-alkenyl, $C_3$-$C_4$-alkynyl or cyclopropyl,
$R^5$ is $C_3$-$C_{18}$-alkyl, $C_3$-$C_{18}$-alkenyl or $C_3$-$C_{18}$-alkynyl which is unsubstituted or monosubstituted to trisubstituted by $C_1$-$C_8$-alkoxy, $C_5$-$C_{12}$-cycloalkyl or $C_5$-$C_{12}$-cycloalkenyl which is unsubstituted or monosubstituted to trisubstituted by $C_3$-$C_8$-alkyl, $C_3$-$C_8$-alkenyl or $C_3$-$C_8$-alkoxy,
or $R^5$ is a radical

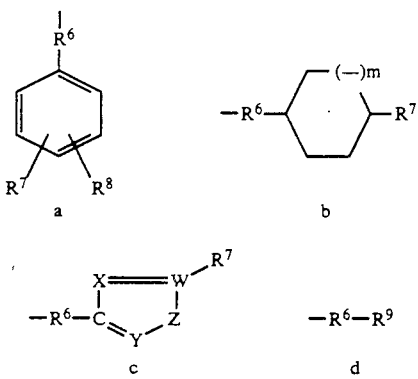

a    b

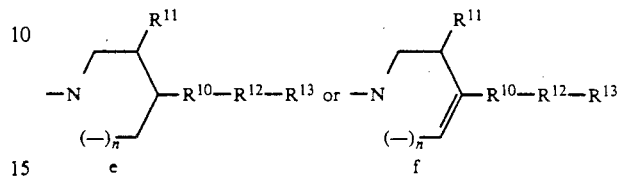

c    d where $R^6$ is $C_1$–$C_5$-alkylene or $C_1$–$C_5$-alkenylene,
$R^7$ is $C_3$–$C_8$-alkyl, $C_3$–$C_8$-alkenyl, $C_3$–$C_8$-alkoxy, $C_1$–$C_3$-alkoxy-$C_2$–$C_5$-alkyl, $C_3$–$C_5$-alkylthio or trimethylsilyl,
$R^8$ is H or $CH_3$,
$R^9$ is $C_6$–$C_{10}$-bicycloalkyl or $C_6$–$C_{10}$-bicycloalkenyl which is unsubstituted or substituted by 2 or 3 methyl groups,
W, X, Y and Z are each a ring atom in an aromatic 5-membered heterocyclic ring, i.e., 1 or 2 radicals from the group consisting of O, S, N, NH, N—$R^7$ and 2 or 3 radicals CH and C—$R^7$,
m is 0, 1 or 2, so that the radical 5b contains a cyclohexyl, cycloheptyl or cyclopentyl radical,
$R^4$ and $R^5$, together with the nitrogen atom on which they are substituents, may furthermore form a 5-membered or 6-membered ring e or f e    f where $R^{10}$ is H or $(CH_2)_q$, in which q is 0, 1, 2, 3 or 4 or methyl, ethyl or branched $C_3$–$C_8$-alkyl,
$R^{11}$ is H or $C_1$–$C_5$-alkyl,
$R^{12}$ is H or phenyl when $R^{10}$ is not H,
$R^{13}$ is $C_3$–$C_6$-alkyl when $R^{12}$ is phenyl,
n is 0 or 1, so that the radical 5e or 5f contains a 6-membered or 5-membered heterocyclic ring,
or a plant-tolerated salt or N-oxide thereof, is allowed to act on the fungi, or the materials, areas, plants or seed threatened by fungus attack.

* * * * *